US008187875B2

(12) United States Patent
Ravindran et al.

(10) Patent No.: US 8,187,875 B2
(45) Date of Patent: May 29, 2012

(54) DOPAMINERGIC NEURONS DERIVED FROM CORNEAL LIMBUS, METHODS OF ISOLATION AND USES THEREOF

(75) Inventors: Geeta Ravindran, Maharashtra (IN); Harinarayana Rao, Maharashtra (IN)

(73) Assignee: Reliance Life Sciences Pvt. Ltd., Rabale, Navi Mumbai (IN)

( * ) Notice: Subject to any disclaimer, the term of this patent is extended or adjusted under 35 U.S.C. 154(b) by 32 days.

(21) Appl. No.: 11/502,338

(22) Filed: Aug. 10, 2006

(65) Prior Publication Data
US 2007/0020247 A1 Jan. 25, 2007

Related U.S. Application Data

(63) Continuation-in-part of application No. 11/063,335, filed on Feb. 22, 2005.

(60) Provisional application No. 60/621,476, filed on Oct. 22, 2004.

(51) Int. Cl.
C12N 5/071 (2010.01)
(52) U.S. Cl. ......... 435/371; 435/325; 435/363; 435/366
(58) Field of Classification Search .................. None
See application file for complete search history.

(56) References Cited

U.S. PATENT DOCUMENTS

| 6,152,142 | A | 11/2000 | Tseng |
| 6,200,806 | B1 | 3/2001 | Thomson |
| 6,610,538 | B2 | 8/2003 | De Luca et al. |
| 6,897,060 | B1 * | 5/2005 | Bjornson et al. ............ 435/325 |
| 6,921,665 | B2 | 7/2005 | McWhir et al. |
| 2002/0039788 | A1 | 4/2002 | Isseroff et al. |
| 2003/0161817 | A1 | 8/2003 | Young et al. |
| 2003/0186439 | A1 | 10/2003 | Nakauchi et al. |
| 2003/0208266 | A1 | 11/2003 | Tsai |
| 2003/0235563 | A1 | 12/2003 | Strom et al. |
| 2004/0018617 | A1 | 1/2004 | Hwang |
| 2004/0033214 | A1 | 2/2004 | Young et al. |
| 2005/0136536 | A1 | 6/2005 | Anderson et al. |

FOREIGN PATENT DOCUMENTS

| EP | 0572364 A2 | 12/1993 |
| EP | 0572364 A3 | 12/1993 |
| WO | WO 00/73421 A2 | 12/2000 |
| WO | WO 00/73421 A3 | 12/2000 |
| WO | WO 03/030959 A1 | 4/2003 |
| WO | WO 03/093457 A1 | 11/2003 |

OTHER PUBLICATIONS

Carpenter et al. Exp Neurol. 1999;158,265-78.*
Studer et al. Nat Neurosci 1998;1:290-5.*
Harkin et al. Br J Ophthalmol 2004;88:1154-8.*
Abeyta, et al., *Unique Gene Expression Signatures of Independently-derived Human Embryonic Stem Cell Lines*, Hum. Mol. Genet., 13:6:601-608, 2004.
Alison and Sarraf, *Hepatic Stem Cells*, J. of Hepatol., 29:676-682, 1998.
Cotsarelis, et al., *Existence of Slow-Cycling Limbal Epithelial Basal Cells that can be Preferentially Stimulated to Proliferate: Implications on Epithelial Stem Cells*, Cell, 57:201-209, 1989.
Furusawa, et al., *Embryonic Stem Cells Expressing Both Platelet Endothelial Cell Adhesion Molecule-1 and State-Specific Embryonic Antigen-1 Differentiate Predominantly into Epiblast Cells in a Chimeric Embryo*, Biol. of Reprod., 70:1452-1457, 2004.
Gage, F.H., *Mammalian Neural Stem Cells*, Science, 287:1433-1438, 2000.
Gearhart, J., *New Potential for Human Embryonic Stem Cells*, Science, 282:1061-62, 1998.
Henderson, et al., *The Long Term Outcome of Limbal Allowgrafts: The Search for Surviving Cells*, Br. J. Ophthalmol., 85:604-609, 2001.
Howell, et al., *Pluripotent Stem Cells Identified in Multiple Murine Tissues*, Ann. N.Y. Acad. Sci., 996:158-173, 2003.
Hu and Aunins, *Large-scale Mammalian Cell Culture*, Curr. Opin. Biotechnol., 8:148-153, 1997.
Jiang, et al., *Pluripotency of Mesemchymal Stem Cells Derived from Adult Marrow*, Nature, 418:41-48, 2002.
Li, et al., *Pluripotent Stem Cells from the Adult Mouse Inner Ear*, Nature Med., 9(10)1293-1299, 2003.
Moore, et al., *The Corneal Epithelial Stem Cell*, DNA and Cell Biol., 21(5/6)443-51, 2002.
Pelligrini, et al., *p63 Identifies Keratinocyte Stem Cells*, Proc. Natl. Acad. Sci. USA, 98(6)3156-61, 2001.
Pittenger, et al., *Multilineage Potential of Adult Human Mesenchymal Stem Cells*, Science, 284:143-147, 1999.
Potten, *Stem Cells in Gastrointestinal Epithelium: Numbers, Characteristics and Death*, Phil. Trans. R. Soc. Lond. B., 353:821-830, 1998.
Prusa, et al., *Oct-4-Expressing Cells in Human Amniotic Fluid: a New Source for Stem Cell Research?*, Hum. Reprod., 18(7)1489-1493, 2003.
Reubinoff, et al., *Embryonic Stem Cell Lines from Human Blastocysts: Somatic Differentiation in vitro*, Nature Biotech., 18:399-403, 2000. Schermer, et al., *Differentiation-related Expression of a Major 64K Corneal Keratin In Vivo and in Culture Suggests Limbal Location of Corneal Epithelial Stem Cells*, J. Cell Biol., 103:49-62, 1986.
Seigel, et al., *Human Corneal Stem Cells Display Functional Neuronal Properties*, Mol. Vis., 9:159-63, 2003.
Spier, *Large-scale Mammalian Cell Culture: Methods, Applications and Products*, Curr. Opin. Biotechnol., 2:375-79, 1991.
Thomson, et al., *Embryonic Stem Cell Lines Derived from Human Blastocysts*, Science, 282:1145-1147, 1998.

(Continued)

Primary Examiner — Q. Janice Li
(74) Attorney, Agent, or Firm — Vinson & Elkins LLP

(57) ABSTRACT

The present disclosure describes the generation of neural cells and neurons from mammalian pluripotent embryonic-like stem cells (ELSCs) isolated from corneal limbal tissue, a non-embryonic tissue. Specifically, the present disclosure describes the generation of neuroprogenitor cells and differentiated dopaminergic neurons from ELSCs. The disclosed methods demonstrate the potential of ELSCs as a therapeutic tool, and may provide new therapeutic alternatives for various diseases, conditions, and injuries. Neuroprogenitor cells generated from ELSCs isolated from corneo-limbal tissue were transplanted into a rat model of Parkinson's disease, and were able to alleviate motor abnormalities in the rats for at least six months.

3 Claims, 8 Drawing Sheets

OTHER PUBLICATIONS

Toma, et al., *Isolation of Multipotent Adult Stem Cells from the Dermis of Mammalian Skin*, Nat. Cell. Biol., 3:778-84, 2001.
Tsai, et al., *Reconstruction of Damaged Corneas by Transplantation of Autologous Limbal Epithelial* Cells, N. Engl. J. Med., 343:(2)86-93, 2000.
Tseng, *Regulation and Clinical Implications of Corneal Epithelial Stem* Cells, Mol. Biol. Rep., 23:47-58, 1996.
Tseng, et al., *Amniotic Membrane Transplantation With or Without Limbal Allografts for Corneal Surface Reconstruction in Patients with Limbal Stem Cell* Deficiency, Arch. Ophthalmol., 116:431-41, 1998.
Watt, *Epidermal Stem Cells: Markers, Patterning and the Control of Stem Cell Fate*, Phil. Trans. R. Soc. Lond. B., 353:831-837, 1998.
Weissman, *Translating Stem and Progenitor Cell Biology to the Clinic: Barriers and Opportunities*, Science, 287:1442-1446, 2000.
Wells, et al., *Cytokeratin 18 is Expressed on the Hepatocyte Plasma Membrane Surface and Interacts with Thrombin-Antithrombin Complexes*, J. Biol. Chem., 272(45)28574-28581, 1997.
Xu, et al., *Feeder-free Growth of Undifferentiated Human Embryonic Stem Cells*, Nat. Biotechnol, 19:971-4, 2001.
Young, et al., *Clonogenic Analysis Reveals Reserve Stem Cells in Postnatal Mammals. II. Pluripotent Epiblastic-Like Stem Cells*, Anat. Rec., 277A(1):178-203, 2004.
Aldhous and Reich, "Flawed Stem Cell Data Withdrawn", New Scientist, Feb. 15, 2007.
Anderson, et al., "Amniotic Membrane Transplantation for Partial Limbal Stem Cell Deficiency", Br. J. Ophthalmol. 85:567-575, 2001.
Andrews, et al., "Embryonic Stem (ES) Cells and Embryonal Carcinoma (EC) Cells: Opposite Sides of the Same Coin", Biochem. Soc. Trans. 33:1526-1530. 2005.
Ausubel, et al., "Techniques for Mammalian Cell Tissue Culture", Current Protocols in Molecular Biology, 4:Appendix 3F, pp. A.3F.1-A.3F.10, 1994.
Deschambeault, et al., "In vitro Characterization of Human Limbal Epithelial Cells Isolated From the Four Quandrants", ARVO Annual Meeting Abstract Search and Program Planner, vol. 2003, Abstract No. 1357, 2003.
Du, et al., "Functional Reconstruction of Rabbit Corneal Epithelium by Human Limbal Cells Cultured on Amniotic Membrane", Mol. Vis. 9:635-643, 2003.
Dua, et al., "Limbal Stem Cells of the Corneal Epithelium", Surv. Ophthalmol. 44:415-425, 2000.
Grueterich, et al., "Connexin 43 Expression and Proliferation of Human Limbal Epithelium on Intact and Denuded Amniotic Membrane", Invest. Ophthalmol. Vis. Sci. 43:63-71, 2002.
Herbert, in "Immunobiology", Fifth Edition, Appendix II (Janeway, et al., eds., Garland Science, London, United Kingdom, 2001).
Holland, et al., "Epithelial Transplantation for the Management of Severe Ocular Surface Disease", Trans. Am. Ophthalmol. Soc. 94:677-743, 1996.
Koestenbauer, et al., "Embryonic Stem Cells: Similarities and Differences Between Human and Murine Embryonic Stem Cells", Am. J. Reprod. Immunol. 55:169-180, 2006.
Koizumi, et al., "Amniotic Membrane as a Substrate for Cultivating Limbal Corneal Epithelial Cells for Autologous Transplantation in Rabbits", Cornea 19:65-71, 2000.
Koizumi, et al., "Cultivated Corneal Epithelial Stem Cell Transplantation in Ocular Surface Disorders", Ophthalmology 108:1569-1574, 2001.
Koizumi, et al., "Cultivation of Corneal Epithelial Cells on Intact and Denuded Human Amniotic Membrane", Invest. Ophthalmol. Vis. Sci. 41:2506-2513, 2000.
Lindstrom, "Advances in Corneal Transplantation", N. Engl. J. Med. 315:57-59, 1986.
McCloskey, et al., "Magnetophoretic Cell Sorting is a Function of Antibody Binding Capacity", Biotechnol. Prog. 19:899-907, 2003.
Moreadith and Radford, "Gene Targeting in Embryonic Stem Cells: The New Physiology and Metabolism", J. Mol. Med. 75:208-216, 1997.
Odorico, et al., "Multilineage Differentiation from Human Embryonic Stem Cell Lines", Stem Cells 19:193-204, 2001.
PCT/IB2005/00203, International Search Report, Feb. 28, 2007.
Pellegrini, et al., "Long-term Restoration of Damaged Corneal Surfaces with Autologous Cultivated Corneal Epithelium", Lancet 349:990-993, 1997.
Pera, et al., "Human Embryonic Stem Cells", J. Cell Sci. 113:5-10, 2000.
Pincock, "Adult Stem Cell Report Questioned", The Scientist, Feb. 26, 2007.
Prabhasawat, et al., "Impression Cytology Study of Epithelial Phenotype of Ocular Surface Reconstructed by Preserved Human Amniotic Membrane", Arch. Ophthalmol. 115:1360-1367, 1997.
Serafini and Verfaillie, "Pluripotency in Adult Stem Cells: State of the Art", Semin. Reprod. Med. 24:379-388, 2006.
Shimazaki, et al., "Amniotic Membrane Transplantation for Ocular Surface Reconstruction in Patients with Chemical and Thermal Burns", Ophthalmology 104:2068-2076, 1997.
Shimazaki, et al., "Transplantation of Human Limbal Epithelium Cultivated on Amniotic Membrane for the Treatment of Severe Ocular Surface Disorders", Ophthalmology 109:1285-1290, 2002.
Tan, et al., "Limbal Transplantation", Ophthalmology 103:29-36, 1996.
Theise, "On Experimental Design and Discourse in Plasticity Research", Stem Cell Rev. 1:9-13, 2005.
Tsai, et al., "Comparison of Limbal and Conjunctival Autograft Transplantation in Corneal Surface Reconstruction in Rabbits", Ophthalmology 97:446-455, 1990.
Tseng, et al., "Amniotic Membrane Transplantation for Conjunctival Surface Reconstruction", Am. J. Ophthalmol. 124:765-774, 1997.
Ulloa-Montoya, et al., "Culture Systems for Pluripotent Stem Cells", J. Biosci. Bioeng. 100:12-27, 2005.
Wolosin, et al., "Ocular Surface Epithelial and Stem Cell Development", Int. J. Dev. Biol. 48:981-991, 2004.
Xiong, et al., Culture Above Feeder 3T3 Cells in Serum-complemented, Reduced [Ca2+] Medium Allows Generation of Undifferentiated Confluent Monolayers of Limbal Epithelial Cells, Invest. Ophthalmol. Vis. Sci. 40:S324 (Abstract 1718-B626), 1999.
Zhao, et al., "Adult Corneal Limbal Epithelium: A Model for Studying Neural Potential of Non-Neural Stem Cells/Progenitors", Dev. Biol. 250:317-331, 2002.
U.S. Appl. No. 11/043,019, Office Action mailed Aug. 9, 2006.
U.S. Appl. No. 11/043,019, Response filed Nov. 10, 2006 to Office Action mailed Aug. 9, 2006.
U.S. Appl. No. 11/043,019, Office Action mailed Jan. 31, 2007.
U.S. Appl. No. 11/043,019, Response field Apr. 30, 2007 to Office Action mailed Aug. 9, 2006.
U.S. Appl. No. 11/043,019, Office Communication mailed Jun. 6, 2007.
U.S. Appl. No. 11/043,019, Office Action mailed Aug. 24, 2007.
U.S. Appl. No. 11/043,019, Response filed Jan. 24, 2008 to Office Action mailed Aug. 24, 2007.
U.S. Appl. No. 11/043,019, Office Action mailed Apr. 15, 2008.
U.S. Appl. No. 11/063,335, Office Action mailed Apr. 5, 2007.
U.S. Appl. No. 11/063,335, Response filed Sep. 5, 2007 to Office Action mailed Apr. 5, 2007.
U.S. Appl. No. 11/063,335, Office Action mailed Nov. 30, 2007.
U.S. Appl. No. 11/063,335, Response filed May 30, 2008 to Office Action mailed Nov. 30, 2007.

* cited by examiner

DOPAMINERGIC NEURONS DERIVED FROM CORNEAL LIMBUS, METHODS OF ISOLATION AND USES THEREOF

CROSS REFERENCE TO RELATED APPLICATIONS

This application is a continuation-in-part of U.S. Ser. No. 11/063,335, filed Feb. 22, 2005, which claims priority to Indian Application 240/MUM/2004, filed Feb. 26, 2004, and claims the benefit of U.S. Provisional No. 60/621,476, filed Oct. 22, 2004, and also claims priority to PCT/IB2005/000516, filed Feb. 23, 2005, each of which are hereby incorporated by reference in its entirety for all purposes.

STATEMENT REGARDING FEDERALLY SPONSORED RESEARCH OR DEVELOPMENT

Not applicable.

INCORPORATION-BY-REFERENCE

The Sequence Listing file "REL4944004CIPUS_ST25.txt" is hereby incorporated by reference into the present specification in its entirety.

BACKGROUND OF THE INVENTION

1. Field of the Invention

The present disclosure relates to the generation of neural cells, most preferably human dopaminergic neurons, derived from embryonic-like stem cells isolated from corneal limbus tissue. In particularly preferred embodiments, the dopaminergic neurons disclosed herein are used for cell-replacement therapy in various neurodegenerative diseases including, but not limited to, Parkinson's disease. Methods for generating and isolating neural precursor cells and methods for their use are also disclosed.

2. Description of Related Art

I. Stem Cells

In early development, the ultimate source of all tissues in a mammalian embryo or fetus is the stem cell population. In the embryonic stage, embryonic stem cells (ES cells) are totipotent and therefore capable of developing into all the cells of a complete organism. Cellular development occurs through several phases, including cellular proliferation, lineage commitment, and lineage progression, resulting in the formation of differentiated cell types. There are three main lineages that are derived from embryonic germ layers: ectoderm, mesoderm, and endoderm. The ectoderm germ layer forms the epidermis of the skin, sense organs, nervous system, and spinal cord. The mesoderm germ layer forms smooth muscle, connective tissues, blood vessels, heart, blood cells, bone marrow, reproductive organs, the excretory system, striated muscles, and skeletal muscles. Finally, the endoderm germ layer forms epithelial linings of the respiratory and gastrointestinal tracts, including the pharynx, esophagus, stomach, intestine, and other associated organs. ES cells are often referred to as pluripotent stem cells because they are not fixed in their developmental potentialities and can differentiate into many different cell types in vitro.

Because ES cells are capable of becoming almost all of the specialized cells of the body, they have the potential to generate replacement cells for a broad array of tissues and organs such as heart, pancreas, nervous tissue, muscle, cartilage, and the like. ES cells can be derived from the inner cell mass (ICM) of a blastocyst, which is a stage of embryo development that occurs prior to implantation. ES cells derived from the ICM can be cultured in vitro and, under the appropriate conditions, proliferate indefinitely. ES cell lines have been successfully established for a number of species, including mouse (Evans et al., 1981, Nature 292:154-156), rat (Iannaccone et al., 1994, Dev. Biol., 163:288-292), rabbit (Giles et al., 1993, Mol. Reprod. Dev. 36:130-138; Graves et al., 1993, Mol. Reprod. Dev. 36:424-433), hamster (Doetschman et al., 1988, Dev. Biol. 127:224-227), primate (U.S. Pat. No. 5,843,780), and human (Thomson et al., 1998, Science 282:1145-1147; Reubinoff et al., 2000, Nature Biotech. 18:399-403).

The isolation of human ES cells offers the promise of a remarkable array of novel therapeutics. Biologic therapies derived from such cells, including tissue regeneration and repair, as well as targeted delivery of genetic material, are expected to be effective in the treatment of a wide range of medical conditions. Despite the enormous potential of these materials, however, serious ethical issues related to the use of human pluripotent stem cells derived from human embryos or from fetal tissue obtained from terminated pregnancies make stem cell research and treatments involving stem cells controversial. In addition, there are technical issues associated with the use of ES cells. For example, tissues or cells derived from ES cells are not ideal for use in medical treatments because ES cells will generally not be derived from the patient who will ultimately receive the treatment. It is well-known that the use of autologous tissues is preferred for transplant therapies in order to avoid tissue rejection problems, which may prove difficult in the area of stem-cell-based therapies.

The problems associated with human ES cells led many researchers to turn their attention to adult tissues as a possible source of undifferentiated stem cells with properties similar to those of ES cells or germ cells derived from fetal tissue. It is known that after birth and throughout adulthood, a small number of specialized stem cells are retained in an organism for the replacement of cells and the regeneration of tissues. These adult stem cells (also referred to as "tissue-specific stem cells") have been found in very small numbers in various tissues of the adult body, including bone marrow, (Weissman, 2000, Science 287:1442-1446), neural tissue (Gage, 2000, Science 287:1433-1438), gastrointestinal tissue (Potten, 1998, Phil. Trans. R. Soc. Lond. B. 353:821-830), epidermal tissue (Watt, 1997, Phil. Trans. R. Soc. Lond. B. 353:831), hepatic tissue (Alison and Sarraf, 1998, J. Hepatol. 29:678-683), and mesenchymal tissue. (Pittenger et al., 1999, Science 284:143-147).

While some potential sources of adult stem cells have been identified, to date, adult stem cells have not been found to be an adequate replacement for ES cells. First, adult stem cells can be difficult to isolate because they are usually present only in minute quantities in tissues that are often not easily accessible, and their numbers appear to decrease with age. Second, adult stem cells appear to be a less desirable source of cultured tissue than ES cells because they have a shorter life span and less capacity for self-renewal. Third, adult stem cells are believed to be tissue-specific and not pluripotent, generally capable of giving rise only to new cells of a few types closely related to their tissue of origin.

One particularly notable difference between ES cells and adult stem cells is that ES cells in suspension culture are capable of forming aggregates of cells known as embryoid bodies. These embryoid bodies usually contain germ cells of all three lineages that differentiate into various lineage-committed tissues. Therefore, embryoid bodies can be useful in the preparation of different types of differentiated cells in culture. To date, no other isolated adult stem cell lines have been reported that are capable of forming structures similar to embryoid bodies in culture.

Recently, however, it has been suggested that some adult stem cells have the capacity to be pluripotent. The most fully characterized are hematopoietic stem cells known as bone marrow stromal cells or mesenchymal stem cells (Jiang et al., 2002, Nature 418:41-48). These are the first adult stem cells found to have pluripotent properties. Pluripotent adult stem cells have also been isolated from liver (U.S. Publ. No. 2003/0186439), mouse inner ear (Li and Heller, 2003, Nat. Med. 9:1293-1299), and amniotic fluid (Prusa et al., 2003, Hum. Reprod. 18:1489-1493). Recently, pluripotent adult stem cells have been described in many tissues such as skeletal muscle, brain, and intestinal epithelium (Howell et al., 2003, Ann. N.Y. Acad. Sci. 996:158-173.). Still, while these papers report isolated or identified adult stem cells that are pluripotent, these "pluripotent" adult stem cells, unlike ES cells, differentiate into only a few lineages. In addition, none of the isolated adult stem cells reported to date appear to be capable of forming embryoid-like bodies in culture in a manner similar to ES cells.

Similar to the other sources of adult stem cells referenced above, it is known that adult stem cells are present in the corneoscleral limbus of the eye. These cells participate in the dynamic equilibrium of the corneal surface and replace superficial epithelial cells that are shed and sloughed off during eye-blinking. Severe damage to the limbal stem cells from chemical or thermal burns, contact lenses, severe microbial infection, multiple surgical procedures, cryotherapy, or diseases such as Steven-Johnson syndrome or ocular cicatricial pemphigoid can lead to destruction of limbal stem cells and limbal stem cell deficiency, which can lead to an abnormal corneal surface, photophobia, and reduced vision (Anderson et al., 2001, Br. J. Opthalmol. 85:567-575). This damage cannot be repaired without the reintroduction of a source of limbal stem cells (Tseng et al., 1998, Arch. Ophthalmol. 116:431-41; Tsai et al, 2000, N. Engl. J. Med. 343:86-93; Henderson et al., 2001, Br. J. Ophthalmol. 85:604-609).

Experiments conducted in the 1980's first indicated the existence of limbal stem cells in the corneal epithelium (Schermer et al., 1986, J. Cell Biol. 103:49-62; Cotsarelis et al., 1989, Cell 57:201-209). Although it was later suggested that the transcription factor p63 was a specific marker for human corneal stem cells, this marker is also expressed in other epithelial cells such as skin, and therefore is not specific to corneal stem cells. In addition, although p63 expression has been shown to be principally limited to the basal limbal region in human corneas (Moore et al., 2002, DNA Cell Biol. 21:443-51), expression of this transcription factor in mice was maximal in paracentral cornea tissue rather than limbus (Moore et al., 2002, DNA Cell Biol. 21:443-451). Therefore, there is currently no known definitive stem cell marker for limbal epithelial stem cells.

It would be desirable to identify a source of adult stem cells that are capable of self-renewal in culture and are pluripotent and ES cell-like in their ability to differentiate into cells of all three major lineages: ectoderm, mesoderm, and endoderm. Further, it would be desirable to isolate and culture these adult stem cells, and to induce them to differentiate into various cell types, such as, for example, neuronal cells.

II. Neurodegenerative Disorders

Neurodegenerative disorders and neuronal diseases such as Parkinson's disease, Alzheimer's disease, and schizophrenia are destructive diseases that are becoming ever more prominent in our society. Many of these neurological disorders are associated with dopaminergic neurons. Dopaminergic neurons reside in the ventral and ventro-lateral aspects of the midbrain, and control postural reflexes, movement, and reward-associated behaviors. These neurons innervate multiple structures in the forebrain, and their degeneration or abnormal function is associated with Parkinson's disease, schizophrenia, and drug addiction (Hynes et al., 1995, Cell 80:95-101).

Parkinson's disease is a progressive neurological disorder caused by the degeneration of neurons in the region of the brain that controls movements. This degeneration creates a shortage of dopamine, causing the movement impairments that characterize the disease. Pathological studies indicate that loss of dopaminergic neurons in the substantia nigra contributes to Parkinson's disease (Ungerstedt, 1971, U. Acta Physiol. Scand. Suppl. 367:95-121; Yirek and Sladek, 1990, Annu. Rev. Neurosci. 13:415-440). In parkinsonism, changes in the status of dopaminergic receptors may be dependent on the stage of progression of the disease. The hallmark of parkinsonism is a severe reduction of dopamine in all components of the basal ganglia (Hornykiewicz, 1988, Mt. Sinai J. Med. 55:11-20). When dopamine is depleted, various other areas in the brain such as the thalamus, globus pallidus, and the subthalamic nucleus start to malfunction. Since these areas send signals to other parts of the brain, malfunctions in these small areas can lead to widespread brain dysfunction.

The prevalence of Parkinson's disease varies widely from 82 per 100,000 in Japan and 108 per 100,000 in UK, to nearly 1% (approximately 1 million) of the population in North America. In India, the prevalence rate of Parkinson's disease is 14 per 100,000 in North India, 27 per 100,000 in South India, 16 per 100,000 in East India, and 363 per 100,000 for the Parsi community in Western India. While Parkinson's disease is currently considered incurable, a variety of medications are available that provide symptomatic relief from Parkinson's disease, including Levodopa, Bromocriptine, pergolide, selegiline, anticholinergic, and amantadine. Although these drugs may provide relief from the symptoms of Parkinson's disease, they often have significant side effects. Moreover, these drugs neither cure the disease nor slow down the progressive loss of neurons, and only relieve the symptoms, with the beneficial effects often wearing off with time.

These unsatisfactory outcomes have promoted the development of other strategies for treating this disease, such as dopa-receptor agonist therapy and surgical approaches that include pallidotomy, deep brain stimulation (DBS) of the globus pallidus, and attempts to interrupt network abnormalities by destroying overactive brain areas or placing DBS electrodes to quiet these areas. Although these and other surgeries have produced some beneficial results in patients with Parkinson's disease, the long-term effects of such surgeries are not yet known. These treatments also have certain limitations and side effects. Because of the limitations of current treatments, several new strategies are being pursued to develop novel therapies for patients with Parkinson's disease. These techniques range from the use of dopaminotrophic factors (Takayama, et al., 1995, Nature Med. 1:53-58) and viral vectors (Choi-Lundberg et al., 1997, Science 275:838-841) to the transplantation of primary xenogeneic tissue (Deacon et al, 1997, Nature Med. 3:350-353). In addition, gene therapy is being pursued as a therapeutic strategy for this disease (Zurn et al., 2001, Brain Res Rev. 36:222-229; Date et al., 2001, Cell Transplant 10:397-401; Akerud et al., 2001, J. Neurosci. 21:8108-8118).

Cell implantation is another therapeutic strategy that offers the hope of replacing nerve cells lost in Parkinson's disease, as well as other neurodegenerative disorders and neuronal diseases. Clinical trials with fetal tissue transplantation, still underway, have demonstrated methods for implanting cells into the brain and the viability of this concept, as well as produced promising results for at least some patients (Freed et al., 2001, N. Engl. J. Med. 344:710-719; Winkler et al., 2000, Prog. Brain Res. 127:233-265). In one study, transplantation of dopaminergic neurons into the substantia nigra of a patient with Parkinson's disease was described as therapeutically effective, but symptomatic relief was incomplete (Lindvall, 1997, Neuroreport. 8(14):iii-x), indicating that transplantation of dopaminergic neurons alone may not be sufficient to cure Parkinson's disease.

Recently, a renewable source of neural stem cells was discovered in the adult human brain. Neural stem cells with the capacity to renew themselves and form all cell types of the brain offer a potentially unlimited supply of dopamine-producing brain cells, thus promising an entirely new therapeutic approach to neurodegenerative disorders and neuronal diseases (Eriksson et al., 1998, Nature Medicine 4:1313-1317). It has been reported that cultures of neural stem cells derived from the embryonic human forebrain can be expanded up to ten million fold in vitro. These adult neural stem cells were transplanted into adult rats that serve as a well-characterized model of Parkinson's disease. The transplanted cells survived for up to a year after transplantation, differentiated into neurons, and improved motor disorders in some of the experimental animals (Svendsen et aL., 1997, Exp. Neurol. 148: 135-146). Unfortunately, adult neural stem cells have a limited life span in tissue culture (Kukekov et al., 1999, Exp. Neurol. 156:333-344).

One viable alternative source of dopaminergic neurons, and other neurons that may be used to treat various neurodegenerative disorders and neuronal diseases, are pluripotent ES cells. Studies have shown that ES cells can be differentiated into neural progenitor cells (Zhang et al., 2001, Nature Biotech. 19:1129-33; WO 01/88104; U.S. Pat. No. 6,833, 269; U.S. Ser. Nos. 09/888,309, 10/157,288; WO 03/000868; each specifically incorporated herein by reference). These cells can then be further differentiated into dopaminergic neurons (Rolletschek et al., 2001, Mech. Dev. 105:93-104, incorporated herein by reference). An initial step in the differentiation of ES cells can be the formation of embryoid bodies; for example, 1 mM of retinoic acid promotes neural differentiation into embryoid bodies (Bain et al., 1995, Dev. Biol. 168:342-357, incorporated herein by reference). While retinoic acid can be used to generate neural cells, retinoic acid is a strong teratogen.

Several reports have been published on the differentiation of ES cells into dopaminergic neurons by using stromal cell inducing activity (SIDA) (Kawasaki et al., 2000, Neuron 28:1-20), by expressing nuclear receptor related-l gene (Nurr-1) (Kim et al., 2002, Nature 418:50-56), or by transplanting undifferentiated ES cells directly into the mouse model (Bjorklund et al., 2002, Proc. Natl Acad. Sci. 99:2344-2349). Lee et al. reported a method for differentiating ES cells into neural progenitor cells and into dopaminergic and serotonergic neurons in vitro (Lee et al., 2000, Nat. Biotechnol. 18:675-79). All of these experiments, however, were carried out using mouse ES cells, and the differentiation protocols yielded dopaminergic neurons ranging from 5-50%. About 20% of the mouse ES cells developed into dopaminergic neurons in the study by Lee et al. (WO 01/83715) and 5-50% in the study by Studer et al. (WO 02/086073). While dopaminergic neurons have also been differentiated from human ES cells, yields of only 5-7% of dopaminergic neurons, as a percentage of total cells in the population, have been obtained (WO 03/000868).

Parkinson's disease is thought to be a particularly suitable clinical target for a cell transplant therapeutic strategy since it is characterized by the selective and gradual loss of dopaminergic neurons in the substantia nigra of the midbrain. The loss of dopamine-producing neurons within this specific brain site leads to abnormal firing of nerve cells that results in patients being unable to control or direct their movements. But one challenge of this approach is that large numbers of dopaminergic neurons are required for cell replacement therapy. Transplantation of dopaminergic neurons is a clinically promising experimental treatment for advanced stage Parkinson's disease. Cell transplantation therapy has been performed on more than 200 patients worldwide (Olanow et al., 1996, Trends Neurosci. 19:102-109). Clinical improvement has been confirmed (Olanow et al., supra and Wenning et al., 1997, Ann. Neurol. 42:95-107), and was correlated to good graft survival and innervation of the host striatum (Kordower et al., 1995, N. Engl. J. Med. 332:1118-1124). Unfortunately, fetal nigral transplantation therapy generally requires human fetal tissue from at least 3-5 embryos to obtain a clinically significant improvement in the patient. This poses an enormous logistical and ethical dilemma. Thus, alternative sources for dopaminergic neurons are being investigated.

For example, dopaminergic neurons have been generated from CNS precursor cells (WO00/005343; and Studer et al., 1998, Nature Neurosci. 1:290-295.). These precursor-derived neurons are functional in vitro and in vivo and restore behavioral deficits in a rat model of Parkinson's disease. Even though the primary mesencephalic CNS stem cell culture can provide differentiated dopaminergic neurons suitable for use in cell therapy for Parkinson's disease, the cell number provided by this method is limited. The percentage of differentiated dopaminergic neurons obtained from expanded mesencephalic precursors decreases as the cells are expanded more than about 10-100 fold. While mesencephalic precursors can generate about 10% to 15% dopaminergic neurons (out of total cell number) after 10-100 fold expansion, when the precursors are expanded 1000 fold, that number drops to only about 1%.

Efficient generation of dopaminergic neurons in culture is of particular interest in view of the therapeutic promise of cell therapy in Parkinson's disease. Because therapies currently available for treating neurological and neurodegenerative diseases are extremely limited, there is great interest in developing alternative therapies. While ES cells can provide an excellent source of dopaminergic neurons, their use is controversial due to ethical issues. Thus, it is desirable to identify an alternate source from which a high yield of clinically acceptable dopaminergic neurons for human clinical application can be generated. The present disclosure provides a method for derivation of dopaminergic neurons from a novel source of pluripotent stem cells isolated from the adult human eye. The therapeutic potential of these differentiated cells for neurodegenerative diseases, such as Parkinson's Disease, is examined.

BRIEF SUMMARY OF THE INVENTION

The present disclosure describes methods for generating a population of cells comprising neural precursor cells and/or terminally differentiated neural cells. Neural precursor cells, which may also be referred to as neuroprogenitor cells herein, can generate progeny that are either neuronal or glial cells, as well as precursors of either neuronal or glial cells. Examples of terminally differentiated neural cells include, but are not limited to, neurons (e.g., dopaminergic, GABAergic, serotonergic, glutamatergic, and motor neurons) and glial cells (e.g., oligodendrocytes, astrocytes). As used herein, the term "differentiation" refers to a process whereby undifferentiated pluripotent stem cells or precursor cells acquire a more specialized fate. The neural precursor cells and terminally differentiated neural cells of the present disclosure are derived from isolated mammalian pluripotent embryonic-like stem cells (ELSCs). In preferred embodiments, the ELSCs are capable of proliferating in an in vitro culture, maintain the potential to differentiate into cells of endoderm, mesoderm or ectoderm lineage in culture, and are capable of forming embryoid-like bodies (ELBs) when placed in suspension culture. In a particularly preferred embodiment, the neural precursor cells or terminally differentiated neural cells are derived from ELSCs, most preferably ELSCs isolated from corneoscleral limbus tissue. The corneoscleral limbus tissue is preferably human tissue. The population of terminally differentiated neural cells preferably comprise neuronal cells, and more preferably comprise dopaminergic cells. In certain embodiments, the population of terminally differentiated neural cells comprise at least about 30%, 40%, 50%, 60%, 70%, 80%, 90%, or 95% dopaminergic neurons, or alternatively differentiated cells that express tyrosine hydroxylase (TH).

Other embodiments of the present disclosure are methods of generating a population of neural precursor cells or terminally differentiated neural cells from ELSCs comprising the following three steps: (a) expanding a culture of ELSCs; (b) culturing the ELSCs to select for cells that are positive for nestin; and (c) differentiating the nestin-positive cells to generate a population of neural precursor cells and/or terminally differentiated neural cells. In a preferred embodiment, this method is used to generate neurons, most preferably dopaminergic neurons, which may be identified based on morphological features and the presence or absence of specified cell markers. For example, dopaminergic neurons may be identified through their expression of TH. The presence or absence of a cell marker may be detected, for example, by immunofluorescence using antibodies directed against the cell marker or by reverse transcriptase polymerase chain reaction (RT-PCR).

In preferred embodiments, the mammalian ELSCs used to generate neural precursor cells or terminally differentiated are human ELSCs isolated from corneoscleral limbus tissue. In certain embodiments, the mammalian ELSCs are expanded in a medium comprising N2 and B27. In another embodiment, the ELSCs may be cultured to generate embryoid-like bodies (ELBs) prior to further differentiation. The nestin-positive cells also may be cultured in a medium comprising N2 and B27 with one or more growth factors, such as retinoic acid, dibutyrl cyclic AMP (db-cAMP), glial cell line-derived neurotrophic factor gene (GDNF), Interleukin-1β (IL-1β), and the like. In yet another embodiment, the nestin-positive cells are sorted by fluorescence-activated cell sorting (FACS) or magnetic-affinity cell sorting (MACS), to enrich for cells that are positive for nuclear cell adhesion molecule (NCAM). Preferably the nestin-positive cells are sorted so that the population of cells comprise at least about 30%, 40%, 50%, 60%, 70%, 80%, 90%, or 95% of the NCAM-positive cells. The nestin-positive cells and/or nestin-positive, NCAM-positive cells may be further differentiated to generate a population of neural precursor cells or terminally differentiated neural cells.

The present disclosure also describes methods for treating a mammal afflicted with a disease, disorder or injury of the nervous system by transplanting a therapeutically effective amount of a population of neural precursor cells and/or terminally differentiated neural cells generated from mammalian pluripotent ELSCs. In preferred embodiments, the mammalian ELSCs are human ELSCs derived from corneoscleral limbus tissue. The neural precursor cells transplanted into the mammal preferably differentiate in vivo. In particularly preferred embodiments, human ELSCs derived from corneoscleral limbus tissue are administered to a human afflicted with a disease, disorder or injury of the nervous system. In embodiments of the present disclosure, the disease, disorder or injury of the nervous system is a neuronal disorder or a neurodegenerative disease such as, for example, Parkinson's disease, Alzheimer's disease, Huntington's disease, amyotrophic lateral sclerosis (ALS), stroke, ischemia, epilepsy, and the like. In a particularly preferred embodiment, the present disclosure describes methods for treating Parkinson's disease by transplanting a therapeutically effective amount of neural precursor cells or terminally differentiated neural cells disclosed herein into a patient afflicted with Parkinson's disease. In preferred embodiments, the neural precursor cells and/or terminally differentiated neural cells are histocompatible with the patient being treated, for example the transplanted cells have essentially the same genome as the patient.

In preferred embodiments, the transplanted cell population comprises neuronal cells such as, for example, dopaminergic neurons or precursors of dopaminergic neurons. In other embodiments, the transplanted cell population may be combined with another population of neural cells, for example GABAergic neurons. In yet another embodiment of the present disclosure, neuronal survival factors are administered to the mammal receiving the disclosed cell transplantation therapies. Most preferably, cell transplantation therapies are administered as pharmaceutical compositions.

The present disclosure further describes methods for identifying compounds that affect survivability and/or function of neural precursor cells or terminally differentiated neural cells generated from mammalian pluripotent ELSCs, most preferably ELSCS isolated from corneoscleral limbus tissue. In one embodiment, this method identifies compounds that affect the survivability and/or function of neuronal cells, such as dopaminergic neurons, serotonergic neurons, GABAergic neurons and the like. In another embodiment, the present disclosure describes methods for identifying neuronal survival factors based on their ability to improve survivability of precursor cells or terminally differentiated neural cells, both in vitro and in vivo.

BRIEF DESCRIPTION OF THE SEVERAL VIEWS OF THE DRAWINGS

The following drawings form part of the present specification and are included to further demonstrate certain aspects of the present disclosure. The present disclosure may be better understood by reference to one or more of these drawings in combination with the detailed description of specific embodiments presented herein.

DETAILED DESCRIPTION OF THE INVENTION

Figure 1:
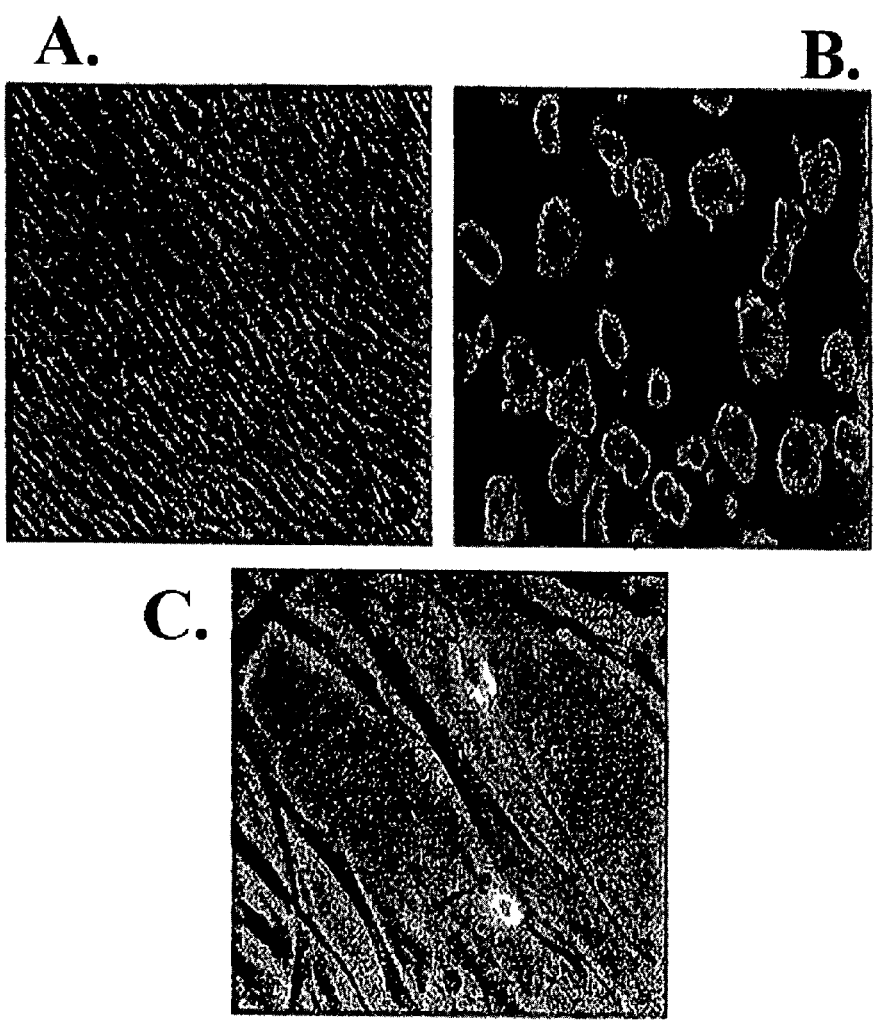
FIG. 1. Phase-contrast micrographs of ELSCs and ELBs (10×): (a) micrograph of passage 15 ELSCs; (b) micrograph of ELBs formed from ELSCs after 4 days of suspension culture; and (c) micrograph demonstrating initiation of differentiation from ELBs formed from ELSCs.

The present discloses relates to the derivation of a population of cells comprising neural precursor cells and/or terminally differentiated neural cells such as, for example, dopaminergic neurons derived from mammalian pluripotent embryonic-like stem cells (ELSCs). ELSCs are isolated from non-embryonic cells or tissues, and have been previously disclosed in U.S. Ser. No. 11/063,335, which is incorporated herein by reference. In preferred embodiments, the present disclosure utilizes mammalian eye structures as a source of ELSCs, preferably corneoscleral or corneal limbus tissue. A significant advantage of the use of such tissue as a source of ELSCs is the relative ease in obtaining corneal limbal tissue from a donor. The process requires only minor surgery that is generally safe and simple, unlike the more invasive procedures that may be used to obtain other types of adult stem cells. The corneoscleral or corneal limbal tissue is found in the cornea, which is a transparent, avascular tissue that is located at the outer surface of the anterior eye.

ELSCs are also capable of forming embryoid-like bodies (ELBs) in culture, for example in suspension culture. As used herein, the terms "embryoid-like bodies" or "ELBs" refer to an aggregation of differentiated cells generated when pluripotent ELSCs are grown in suspension culture, or overgrow in monolayer cultures. ELBs also may have undifferentiated cells in the aggregation of cells. ELBs typically contain cells derived from all three germ layers, ectoderm, mesoderm and endoderm. Functionally, ELBs may be similar or identical to embryoid bodies generated in culture from ES cells, for example human ES cells. Embryoid bodies and ELBs are distinguished from each other in the present disclosure primarily by source; i.e., embryoid bodies are derived from ES cells, while ELBs are derived from ELSCs.

The use of ELSCs as a source of pluripotent stem cells has numerous advantages. First, the use of ELSCs does not raise many of the ethical concerns that are associated with research using cells derived from embryonic or fetal cells and tissue. Second, the use of ELSCs may make autologous pluripotent stem cells available for medical therapies as the source of differentiated cells and tissues without the intermediate step of cloning. It is generally desirable that transplanted cells or tissues be genetically identical to the recipient of the transplant in order to avoid problems with tissue rejection. It is not generally possible, however, to obtain ES cells that are genetically identical to a patient in need of treatment. The use of ELSCs can surmount this problem if the donor of the ELSCs is also the recipient of transplanted cells or tissue derived from the isolated ELSCs.

Corneal limbus (also referred to herein as "corneoscleral limbus" or "corneo-limbus") is an annular transitional zone approximately 1 mm wide between the cornea and the bulbar conjunctiva and sclera. It appears on the outer surface of the eyeball as a slight furrow marking the line between the clear cornea and the sclera. It is highly vascular and is involved in the metabolism of the cornea. Limbal and conjuctival epithelial cells, together with a stable pre-ocular tear film, maintain the integrity of the cornea. While it is known that the source of the replenished corneal epithelial cells is adult stem cells, the exact location and properties of these cells were unknown. The adult stem cells previously isolated from the eye are P-63 positive, and are responsible for maintaining corneal integrity (Pellegrini et al., 2001, Proc. Acad. Natl. Sci. USA, 98:3156-

61). The plasticity of these corneal stem cells was recently reported (Seigel et al., 2003, Mol. Vis. 9:159-63). The existence of a second population of stem cells that are pluripotent and have similar properties to ES cells was unknown.

A typical procedure for isolating corneal limbal tissue is described in U.S. Ser. No. 11/063,335, which is incorporated herein by reference. For example, a small biopsy consisting of 2-3 mm of limbal tissue is surgically removed from the superior or temporal quadrant of the corneal surface of the donor's eye. Procedures for obtaining such biopsies from the corneal limbus are well-known to those of skill in the art. After limbal tissue is biopsied from a donor, it is placed in culture, preferably on an extracellular matrix or bio-coated surface. With bio-coated surfaces, a preferred method of culturing the limbal tissue is to subject the explants to dry incubation for several minutes on a bio-coated tissue culture plate. The explants are then affixed to the tissue culture dish with a small amount of culture medium so that they stick to the bio-coated tissue culture surface. After several hours to a day, media is gently added and cells are incubated for approximately 4-5 days at 37° C. in a $CO_2$ incubator, changing the media every alternate day.

The preferred media used for culturing the cells of the limbal tissue is Dulbecco's Modified Eagles Medium (DMEM) or DMEM:F-12 (1:1), preferably supplemented with a nutrient serum, for example a serum or serum-based solution that supplies nutrients effective for maintaining the growth and viability of the cells (e.g., knock-out serum or heat-inactivated human serum), as well as growth factors. As used herein, the term "growth factor" refers to proteins that bind to receptors on the cell surface, primarily resulting in the activation of cellular proliferation and differentiation. The growth factors used for culturing limbal tissue are preferably selected from EGF, bFGF, LIF, insulin, sodium selenite, human transferrin, or hLIF, as well as combinations thereof. Any suitable culture media known to those of skill in the art may be used. After the limbal cells are cultured for several days, preferably 7 to 21 days or until the cells become confluent, ELSCs can be isolated from the culture. The pluripotent ELSCs can be isolated from the other limbal cells in the culture using a variety of the methods known to those of skill in the art such as immunolabeling and fluorescence sorting, for example solid phase adsorption, FACS, MACS, and the like. Sorting techniques such as immunofluorescence-staining techniques involve the use of appropriate stem cell markers to separate ELSCs from other cells in the culture.

The isolated ELSCs are cultured in an appropriate cell culture medium such as DMEM or DMEM:F-12 medium, preferably supplemented with a nutrient serum, for example a serum or serum-based solution that supplies nutrients effective for maintaining the growth and viability of the cells (e.g., knock-out serum or heat-inactivated human serum), as well as growth factors. In preferred embodiments, the medium is supplemented with growth factors such as EGF, basic FGF, LIF, insulin, transferrin, sodium selenite, and fibronectin. The ELSCs may be cultured on a feeder layer or in feeder-free conditions, such as on an extracellular matrix.

In another embodiment, isolated pluripotent ELSCs are identified and characterized by the ability to form ELBs in culture, for example in suspension culture. Preferably the ELBs can be further cultured to differentiate into cells of ectodermal, mesodermal, and endodermnal lineages. Methods for culturing pluripotent stem cells to generate embryoid bodies are disclosed in U.S. Pat. No. 6,602,711, incorporated herein by reference. These same methods can also be used to generate ELBs from the ELSCs disclosed herein. For example, ELSCs are dissociated using trypsin, and cultured on bacteriological plates that have a non-adhesive surface, thereby preventing attachment of the ELSCs to the surface of the plate. The ELSCs are preferably cultured in an appropriate cell culture medium such as knockout DMEM or DMEM: F-12 medium, preferably supplemented with a nutrient serum, for example a serum or serum-based solution that supplies nutrients effective for maintaining the growth and viability of the cells (e.g., fetal calf serum, fetal bovine serum, knock-out serum, human cord blood serum), as well as growth factors. In preferred embodiments, the medium is supplemented with growth factors such as insulin, transferrin, or sodium selenite. The ELSCs are cultured until they form ELBs. Preferably the ELBs are cultured until they reach sufficient size or desired differentiation, for example after 3-10 days of culture, preferably 4-14 days. When ELBs are subsequently cultured to differentiate into particular cell types, the ELBs are allowed to grow to a sufficient size to facilitate differentiation into the selected cell type. The ELBs may be plated onto a substrate, for example a substrate coated with extracellular matrix components, including but not limited to poly-L-lysine, poly-L-ornithine, laminin, collagen, fibronectin, Matrigel®, or combinations thereof. The ELBs may be plated directly onto a substrate with or without dispersing the cells.

ELSCs disclosed herein can be utilized for various applications, such as therapeutic and diagnostic applications, as well as for in vitro and in vivo assessment and screening of various compounds such as small molecule drugs for their effects on these cells, as well as differentiated cells derived from ELSCs. For example, compounds such as pharmaceutical compounds, solvents, small molecules, peptides, or polynucleotides, as well as environmental factors such as culture conditions or manipulations may be studies for their affects on the phenotype and other characteristics of these cells. The differentiated cells may be either lineage-committed progenitor or precursor cells, or terminally differentiated cells. Examples of differentiated cell types that may be derived from pluripotent ELSCs include but are not limited to neural cells, neuronal cells, glial cells, corneal cells, osteoblasts, chondrocytes, adipocytes, beta-islets, cardiomyocytes, hepatocytes, and the like. The ELSCs and cells and tissues differentiated therefrom of the present disclosure can be used to treat any subject in need of treatment, including but not limited to humans, primates, and domestic, farm, pet, or sports animals, such as dogs, horses, cats, sheep, pigs, cattle, rats, mice, and the like. These cells can also be used to prepare cDNA expression libraries to analyze the expression patterns of ELSCs as well as cells derived therefrom, and to prepare monoclonal or polyclonal antibodies that are specific to markers for the particular cells used, using techniques that are well known to those of skill in the art.

These cells can also be used therapeutically for the benefit of individuals suffering from debilitating diseases, conditions, injuries, and disorders, for example in tissue reconstitution or regeneration in subjects such as human patients. As used herein, the terms "therapeutically," "to treat," "treatment," or "therapy" refer to both therapeutic treatments and prophylactic or preventative measures. For example, those in need of treatment of the cells generated according to the present disclosure include those already with the neurodegenerative disorder or neuronal disease, as well as those in which the neurodegenerative disorder or neuronal disease is to be prevented. Therapeutic treatment includes but is not limited to reducing or eliminating the symptoms of a particular disease, condition, injury or disorder, or slowing or attenuating the progression of, or curing an existing disease or disorder. Subjects in need of such therapy will be treated by a therapeutically effective amount of such cells or tissues to restore or regenerate function. The methods of the present disclosure can be used to treat any mammal in need of treatment. A disorder may be any condition that would benefit from treatment with neuroprogenitor cells, differentiated neural cells, or more than one of these types of cells of the present disclosure.

As used herein, a "therapeutically effective amount" of cells or tissues is an amount sufficient to arrest or ameliorate the physiological effects in a subject caused by the loss, damage, malfunction, or degeneration of particular cell-types or tissue-types, including, but not limited to, mature neurons (e.g., glutamatergic, GABAergic, serotonergic, and dopaminergic neurons), astrocytes, and oligodendrocytes. The therapeutically effective amount of cells or tissues used will depend on the needs of the subject, the subject's age, physiological condition and health, the desired therapeutic effect, the size of the area of tissue that is to be targeted for therapy, the site of implantation, the extent of pathology, the chosen route of delivery, and the treatment strategy. For example, treatment of a disorder affecting a larger region of the brain could require a larger number of cells to achieve a therapeutic effect when compared to a smaller target region. Cells may also be administered to more than one site in a given target tissue, with multiple small grafts of low cell doses. Preferably, these cells or tissues are administered to the patient in a manner that permits the cells or tissue to graft to the intended tissue site and reconstitute or regenerate the functionally deficient area.

The ability to generate neural precursor cells, as well as differentiated neurons and glial cells, from ELSCs isolated from comeo-limbal tissue, as disclosed herein, is of great clinical relevance for transplantation therapy for a variety of neurodegenerative disorders and neuronal diseases. The following is a brief but by no means exhaustive list of human diseases and conditions potentially treatable through the administration of ELSCs or differentiated cells or tissues derived therefrom: neurodegenerative disorders and neuronal diseases such as Parkinson's disease, Alzheimer's disease, Huntington's disease, cerebellar ataxia, progressive supranuclear palsy, amyotrophic lateral sclerosis (ALS), epilepsy, multiple sclerosis, stroke, ischemia, trauma to the nervous system, neurotoxic injury, and spinal cord injury. In some embodiments of the present disclosure, precursors cells or dopaminergic neurons can be used to treat or prevent neurodegenerative disorders and neuronal diseases which are characterized by abnormalities in fast inhibitory synaptic transmissions, neuronal excitability, and rapid changes in mood, such as seizure threshold, anxiety, panic, and response to stress (i.e., the "fight or flight" response), abnormalities in memory, mood, or pain functions, regulation of postural reflexes, movement, and reward-associated behaviors, for example Parkinson's disease, schizophrenia, and drug addiction, as well as lesions due to trauma or other illnesses that result in Parkinson-like conditions such as resting tremor, rigidity, akinesia, and postural abnormalities such as akinesia, adipsia, aphagia and sensory neglect.

In particular embodiments, precursor cells or dopaminergic neurons can be used, perhaps in combination with other neuronal cells such as GABAergic neurons, to treat or prevent Alzheimer's disease, epilepsy, cerebellar ataxia, progressive supranuclear palsy, spinal cord injury, ALS, Huntington's disease, stroke, ischemia, cerebral ischemia, injury or trauma to the nervous system, neurotoxic injury, as well as neurodegenerative disorders and neuronal diseases which are characterized by the degeneration or destruction of the myelin sheath or membrane. Precursors cells or dopaminergic neurons can also used in combination with other neural or neuronal cells to treat or prevent certain neurological disorders including but not limited to disorders associated with cognition and psychology such as anxiety disorders, mood disorders, addiction, obsessive-compulsive disorders (OCD), personality disorders, attention deficit disorder (ADD), attention deficit hyperactivity disorder (ADHD), and schizophrenia. Additionally, serotonergic neurons or oligodendrocytes can be used to treat neurodegenerative disorders or neuronal diseases.

ELSCs of the present disclosure may be induced to differentiate by any appropriate method known to those of skill in the art. Many such methods are well known to those of skill in the art for differentiating ES cells or adult stem cells into specific cell types, for example neuronal precursor cells, neuronal cells, or glial cells (U.S. Pat. Nos. 6,833,269 and 7,011,828; WO 01/88104, WO 03/000868, WO 01/83715, and U.S. Ser. Nos. 09/970,382, 10/157,288, 10/127,740, and 10/258,975), all of which are specifically incorporated herein by reference. Although these methods were originally adapted for differentiating ES cells or adult stem cells into specific cell types, they may also be adapted for differentiating the ELSCs described herein. These methods can include differentiation through the formation of colonies, ELBs, or other aggregates (U.S. Ser. No. 10/632,399 and WO 01/62899, specifically incorporated herein by reference), as well as methods promoting differentiation into certain cell lineages by withdrawing serum or factors that inhibit differentiation and/or adding factors that promote differentiation. Differentiation of cells may also be facilitated by the use of particular extracellular matrices, for example poly-L-ornithine, laminin, or Matrigel™. ELSCs can also be differentiated directly into committed precursor cells or fully differentiated cells, for example without forming ELBs as an intermediate step.

Preferred methods of inducing differentiation of ELSCs include the use of differentiation agents, including but not limited to progesterone, putrescine, laminin, insulin, insulin-transferrin, selenite, sodium selenite, transferrin, neurturin, sonic hedgehog (SHH), noggin, follistatin, retinoic acid, epidermal growth factor (EGF), any type of fibroblast growth factor, cytosine β-d-Arabino furanoside (Ara-C), growth and differentiation factor 5 (GDF-5), members of the neurotrophin family (NGF, neurotrophin 3 (NT-3), neurotrophin 4 (NT-4), brain derived neurotrophic factor (BDNF)), transforming growth factor α (TGF-α), transforming growth factor beta-1 (TGF-β1), transforming growth factor beta-3 (TGF-β3), platelet-derived growth factor (PDGF), IGF-1, bone morphogenic proteins (BMP-2, BMP-4), GDNF, midkine, ascorbic acid, ascorbic acid 2 phosphate, dibutyryl cAMP, dopamine, ligands to receptors that complex with gp130 (e.g., LIF, ciliary neurotrophic factor (CNTF), SCF, IL-11, and IL-6), insulin-transferrin-selenious acid (ITS), dexamethasone, sodium butyrate, dimethyl sulfoxide (DMSO), N-acetyl Cysteine, IGF-I or IGF-II, β glycerophosphate, 5-Aza-deoxy-cytidine, oncostatin, hepatocyte growth factor (HGF), nicotinamide, or combinations thereof. As used herein, the term "fibroblast growth factor" or "FGF" refers to any suitable fibroblast growth factor, derived from any organism that expresses such factors, and fuinctional fragments thereof. A variety of FGFs are known to those of skill in the art, and include but are not limited to, FGF- 1 (acidic fibroblast growth factor), FGF-2 (basic fibroblast growth factor), FGF-3 (int-2), FGF-4 (hst/K-FGF), FGF-5, FGF-6, FGF-7, FGF-8, and FGF-9. Differentiation nutrient mediums may also contain additives that help sustain cultures of neural cells, for example N2 and B27 additives (Gibco). ELSCs can be induced to differentiate in various available culture media, including but not limited to DMEM, DMEM:F-12, Neurobasal medium, neurturin, N2, B27, and the like, or combinations thereof.

The presence of differentiated cells in a cell culture can be determined by any one of many methods known to those of skill in the art. For example, determination of differentiated cells can be accomplished by methods such as flow cytometry, immunochemistry, immunofluorescence staining, or other staining techniques, to detect the presence of cell-surface markers, proteins, or other types of genetic markers. Alternately, identifying differentiated cells may be accomplished by detecting expression of certain genes or gene products such as RNA or proteins using RT-PCR, HPLC, and the like.

One embodiment of the present disclosure is directed to improved methods for generating neurons from ELSCs, which have characteristics of midbrain neurons, such as dopaminergic neurons. These neurons are derived from ELSCs by culturing the cells in the presence of certain soluble factors and environmental conditions. U.S. Ser. No. 10/798,790 discloses the generation of neural precursor cells, neural cells, and neuronal cells from ELSCs, and is incorporated herein by reference in its entirety. The cells differentiated from ELSCs herein include, but are not limited to, cells with the phenotypic characteristics of neuroprogenitor cells, dopaminergic, serotonergic, cholinergic, and sensory neurons, as well as astrocytes and oligodendrocytes. Differentiated cells are identified by phenotypic characteristics, morphological characteristics, and/or cell markers, which are readily appreciated by those of skill in the art of evaluating such cells.

Preferably, a high percentage of the neuroprogenitor cells differentiate, either in vivo or in vitro, into dopaminergic neurons, serotonergic neurons, or oligodendrocytes, for example at least about 20%, 25%, 30%, 35%, 40%, 45%, 50%, 55%, 60%, 65%, 70%, 75%, 80%, 85%, 90%, 95%, or 99% of the cells. In preferred embodiments, the ELSCs are cultured to generate differentiated cell populations, which preferably comprise about 50%, 60%, 70%, 80%, 90%, or 99% neural or neuronal cells; about 30%, 40%, 50%, 60%, 70%, 80%, 90%, or 99% dopaminergic neurons; about 5-10% serotonergic neurons; and/or about 15-20% glial cells, preferably oligodendrocytes. In addition, one neural cell type, for example dopaminergic neurons, may be further purified from a population of differentiated neural cells by methods well known to those of skill in the art, such as immunolabeling and fluorescence sorting, for example solid phase adsorption, FACS, MACS, and the like.

As used herein, the term "neuroprogenitor cell" is interchangeable with the terms "neural progenitor cell" or "neural precursor cell," and refers to a cell that can generate progeny that are either neuronal cells, such as neuronal precursors or neurons, or glial cells, such as glial precursors, astrocytes, or oligodendrocytes. The methods disclosed herein involve culturing ELSCs in a combination of soluble factors and environmental conditions that encourage the ELSCs to differentiate into cells of neural lineage. In addition, physical separation or manipulation techniques can be used to further enrich for a desired neural-cell type. The methods disclosed herein are most preferably used to derive dopaminergic neurons from ELSCs isolated from human corneo-limbal tissue.

The present disclosure is directed to differentiating ELSCs into neuroprogenitor cells, as well as into a differentiated population of neural cells having the phenotypic, molecular, and/or cellular characteristics similar to cells of neural lineage, such as, for example, dopaminergic and serotonergic neurons. As used herein, the term "dopaminergic neurons" refer to neuronal cells that express tyrosine hydroxylase (TH), the rate-limiting enzyme for dopamine synthesis. Preferably dopaminergic neurons secrete the neurotransmitter dopamine, and have little or no expression of dopamine-β-hydroxylase. As used herein, "serotonergic neurons" refer to neurons that secrete the neurotransmitter serotonin (5-hydroxytryptamine). The abnormal function of serotonergic neurons has been linked to aggression, depression (including suicidal behavior), and schizophrenia.

Isolated ELSCs may be expanded and then subjected to culture conditions which cause them to differentiate into neuroprogenitor cells. For ELSCs to advance along the neural differentiation pathway, the cells are cultured according to differentiation protocols for neural differentiation, which are well-known to those of skill in the art. The ELSCs are cultured on a suitable substrate in a differentiation nutrient medium which contains differentiation agents such as soluble factors and growth factors. Suitable substrates include but are not limited to solid-surfaces coated with a positive-charge, for example poly-L-lysine or polyornithine, substrates coated with extracellular matrix components, for example fibronectin, laminin, or Matrigel®, or a combination thereof. Preferred differentiation nutrient mediums are those that support the proliferation, differentiation, and survival of desired neural cell types, and may include one or more suitable differentiation agents. Suitable soluble factors include but are not limited to neurotrophins, mitogens, stem cell factors, growth factors, differentiation factors (e.g TGF-β Superfamily), TGF-β Superfamily agonists, neurotrophic factors, antioxidants, neurotransmitters, and survival factors. Many soluble factors are quite versatile, stimulating cellular division in numerous different cell types, while others are specific to particular cell types.

Suitable differentiation agents that specifically encourage the differentiation of neuronal cell types include but are not limited to progesterone, putrescine, laminin, insulin, sodium selenite, transferrin, neurturin, sonic hedgehog (SHH), noggin, follistatin, EGF, any type of fibroblast growth factor (for example FGF-4, FGF-8, bFGF), growth and differentiation factor 5 (GDF-5), nicotinamide, members of the neurotrophin family (NGF, NT-3, NT-4, BDNF), TGF-α, TGF-β3, PDGF-AA, IGF-1, BMP-2, BMP-4, GDNF, retinoic acid (RA), midkine, ascorbic acid, dibutyryl cAMP, dopamine, and ligands to receptors that complex with gp130 (e.g., LIF, CNTF, SCF, IL-11, and IL-6). Differentiation nutrient mediums may also contain additives that help sustain cultures of neural cells, for example N2 and B27 additives (Gibco).

In certain embodiments, ELSCs may first be induced to form ELBs. ELBs are plated directly onto a suitable substrate with or without an extracellular matrix component such as fibronectin or laminin, and cultured in a suitable differentiation nutrient medium adapted to promote differentiation into neuroprogenitor cells, such as nestin-positive neuroprogenitor cells. Nestin is a cell-marker characteristic of neural-precursor cells. In another embodiment, the ELSCs are first aggregated into a heterogeneous cell population by forming ELBs, for example by culturing the ELSCs in suspension. These cells can be cultured in nutrient medium with or without serum, as well as with one or more of the differentiation agents listed above, to promote differentiation of cells into the ELBs. ELBs may have undifferentiated cells in the aggregation of cells. Preferably this aggregation of cells is surrounded by primitive endoderm. Preferably the differentiation the ELSCs and ELBs are controlled so that specific cell types can be obtained for therapeutic purposes.

The ELBs may be cultured until they reach sufficient size or desired differentiation, for example after 3-10 days of culture, and then plated onto a substrate. Preferably the substrate is coated with extracellular matrix components, including but not limited to poly-l-lysine, poly-l-ornithine, laminin, collagen, fibronectin, Matrigel®, or combinations thereof. Preferably the ELBs are plated directly onto the substrate without dispersing the cells. The ELBs are then cultured under conditions to encourage further differentiation of the plated cells, for example in ITSFn (nestin selection) serum-free defined medium which is selective for nestin-positive cells. The ELSCs may be selected for nestin-positive cells over a period of 5-16 days. Preferably, the ITSFn medium used for expansion of nestin-positive cells is DMEM:F-12, supplemented with one or more growth factors selected from the group consisting of progesterone, putrescine, laminin, insulin, sodium selenite, transferrin, bFGF, SHH, EGF, FGF-2, FGF-8, and BDNF.

This heterogeneous cell population derived from ELSCs, which includes nestin-positive cells, may be subsequently expanded or sorted for enrichment of NCAM-positive cells. The NCAM-positive cells may be subsequently expanded in medium which helps to increase the percentage of neuroprogenitor cells and further induces these cells to adopt more differentiated phenotypes. In certain embodiments, the above methods further include the step of expanding the nestin-positive and/or NCAM-positive neuroprogenitor cells in expansion media, preferably for 3-10 days. As used herein, the term "expand" or "expansion" refers to the process by which the number of cells is increased via cell growth and division. The term "proliferate" may be used interchangeably with "expand" or "expansion." Preferably, the expansion media comprises a minimal essential medium such as DMEM:F12 supplemented with one or more soluble factors such as, for example, N2 supplement, B27 supplement, and a neural-inducing agent. In a preferred embodiment, the neural-inducing agent comprises DMEM:F12 supplemented with N2, B27, DMSO, Butylated hydroxyl anisole, bFGF and forskolin. The expansion medium also may be supplemented with one or more growth factors selected from group consisting of progesterone, putrescine, laminin, insulin, sodium selenite, transferrin, bFGF, SHH, EGF, FGF-2, FGF-8, BDNF, PDGF, IGF-1, CTNF, and NT-3. Additionally, the cells may be plated on a surface that permits adhesion of neural precursor cells, such as surfaces coated with poly-L-lysine, poly-L-ornithine, laminin, collagen, fibronectin, Matrigel®, or combinations thereof.

In another preferred embodiment, the nestin-positive neuroprogenitor cells are plated on a culture dish pre-coated with poly-L-Ornithine/Laminin, fibronectin or a combination of the two. The nestin-positive neuroprogenitor cells may be expanded in culture and serially passed for one or more population doublings. These cells may also be cryopreserved in liquid nitrogen.

In certain embodiments, ELSCs are differentiated into dopaminergic neurons according to one or more of the following steps: (1) A population of ELSCs is isolated. Most preferably, the ELSCs are derived from corneo-limbal tissue of adult human eye. (2) The ELSCs are expanded. (3) The ELSCs are cultured in suspension to generate ELBs. In one embodiment, the ELBs are generated by culturing ELSCs on bacteriological plates. (4) The ELBs are replated on a substrate and incubated in a medium which selects for the desired cell type. Preferably, the ELBs are incubated in serum-free medium to select for neuroprogenitor cells. (5) The cells, preferably neuroprogenitor cells and most preferably nestin-positive cells, may be expanded using expansion medium. Most preferably, nestin-positive neuroprogenitor cells may be expanded in an expansion medium comprising soluble neural-inducing factors, preferably those which promote the dopaminergic phenotype such as N2 and B27. In a preferred embodiment, the expansion medium contains DMEM/F12 medium supplemented with N2, B27, DMSO, butylated hydroxyl anisole, bFGF and forskolin. (6) The cells are further differentiated using appropriate soluble factors. Preferably, neuroprogenitor cells are further differentiated into dopaminergic neurons in medium comprising, for example, DMEM:F12 medium or Neurobasal A medium supplemented with a combination of soluble factors including but not limited to N2, B27, GDNF, retinoic acid, db-cAMP, and IL-1β. In a preferred embodiment, nestin-positive neuroprogenitor cells are expanded for about 20, 30, 40, or 50 days in differentiation medium. (7) The cells are identified by phenotypic characteristics, morphological characteristics, and/or cell markers, which are readily appreciated by those of skill in the art in evaluating and identifying cells. For example, dopaminergic neurons may be identified by the presence of TH and/or dopamine. In addition, the desired differentiated cells may be further purified from a population of differentiated cells by methods well known to those of skill in the art, such as cell sorting. For example, dopaminergic neurons may purified from a population containing dopaminergic neurons in addition to other differentiated neural cells.

In another embodiment, neural cells, most preferably dopaminergic neurons, are generated from ELSCs, most preferably derived from human corneo-limbal tissue, without the formation of ELBs. For example, ELSCs can be plated onto extracellular matrix coated plates, preferably coated with poly-L-ornithine and laminin. The ELSCs are then cultured under conditions to encourage further differentiation of the cells into glial precursors cells. For example, the cells may be cultured in serum-free expansion medium, preferably comprising a minimal essential medium, such as neurobasal medium, supplemented with inducing agents such as N2 and B27. The expansion media also preferably includes one or more growth factors, such as Retinoic acid, db-cAMP and Interleukin-lb. To characterize the differentiated cell types generated according to these methods, overall morphology of the cells may be observed, the presence or absence of neural or neuronal markers may be assessed by immunofluorescence microscopy, or gene expression analysis may be performed via RT-PCR.

The disclosed progenitor cells and differentiated cells generated from ELSCs derived from corneo-limbal tissue may be assessed to determine efficacy, survivability, and functionality. For example, an in vivo transplantation model may be used to study the efficacy, survivability, and functionality of progenitor cells and differentiated cells, as well as identifying methods for improving cell survivability and functionality following transplantation and transplantation methods. These precursor and differentiated neural cells can be used for a number of applications, including therapeutic and experimental applications, as well as in vitro drug development and screening, such as screening a compound for neural cell toxicity or the ability to modulate the function of neuronal cells. The present disclosure contemplates the use of neural precursor cells and/or terminally differentiated neural cells differentiated from ELSCs for cell-based therapies. For example, ELSCs disclosed herein may be induced to terminally differentiate into appropriate cell or tissue types, or to differentiate into appropriate lineage-committed progenitor cells, which can then be administered or transplanted into a mammalian subject for cell replacement therapy or tissue regeneration.

A preferred embodiment of the present disclosure relates to methods of treating neurodegenerative disorders or neuronal diseases characterized by the degeneration or destruction of dopaminergic neurons by administration or transplantation of a therapeutically effective amount of neuroprogenitor cells or dopaminergic neurons derived from ELSCs, preferably derived from human corneo-limbal tissue. Preferably, a human patient suffering from a neurodegenerative disorder or neuronal disease is treated by engrafting a therapeutically effective amount of neuroprogenitor cells and/or differentiated neural cells of the present disclosure into the patient. For therapeutic applications, it is often preferable that populations of precursors or differentiated neural cells are substantially pure of any undifferentiated pluripotent stem cells. In other embodiments, the present disclosure contemplates the coadministration of one or more neuronal survival factors with neuroprogenitor cells or differentiated neural cells of the present disclosure generated from ELSCs to treat, for example, a neurodegenerative disorder or neuronal disease.

The cells of the present disclosure may be completely dissociated before transplantation, such as to create a suspension of single cells, or nearly completely dissociated before transplantation, such as to create small aggregates of cells. The cells may be administered in a manner that allows them to graft or migrate to the intended tissue site and reconstitute or regenerate a functionally deficient area. A suitable range of cells that can be administered to achieve a therapeutic effect can be from about 100 to about 1,000,000 neurons, preferably from about 500 to about 500,000 neurons, or from about 1000 neurons to about 100,000 neurons. Therapeutic concentrations of neural cells administered to a subject can also range from about 10, 100, 500, 1000, 5000, 10,000, 15,000, 20,000, 25,000, 30,000, 35,000, 40,000, 45,000, 50,000, 60,000, 70,000, 80,000, 90,000, 100,000, 150,000, 200,000, 250,000, 300,000, 350,000, 400,000, 450,000 to about 500,000 cells per microliter of a pharmaceutically acceptable carrier. Ranges of concentrations of cells in a carrier include, for example, 100-50,000 cells/µl, 1000-10,000 cells/µl, 5000-25,000 cells/µl, 15,000-45,000 cells/µl, 20,000-50,000 cells/µl, 55,000-200,000 cells/µl, 100,000-40,000 cells/µl, 150,000-50,000 cells/µl, etc. The number of cells grafted into a transplant site will also affect therapeutic efficacy.

The methods of the present disclosure may be advantageously carried out by direct transplantation of neuroprogenitor cells or differentiated neural cells of the present disclosure to the lesioned area. Methods of neuronal transplantation and cell culture are well known to those of skill in the art, e.g., U.S. Pat. No. 5,514,552; Yurek and Sladek, 1990, Annu. Rev. Neurosci. 13:415-440; Rosenthal, 1998, Neuron 20:169-172; Vescovi et al., 1999, J. Neurotrauma 16(8):689-93; Vescovi et al., 1999, Exp. Neuro. 156(1):71-83; Brustle et al., 1999, Science 285:754-56; each specifically incorporated herein by reference. In one embodiment, the dopaminergic neurons of the present disclosure may be implanted in the substantia nigra or striatum of a patient suffering from Parkinson's disease. The cells may be delivered alone or in combination with other factors, for example a neuronal survival factor, and may be delivered along with a pharmaceutically acceptable vehicle.

The present disclosure also provides for pharmaceutical compositions containing the cells which can be administered using a suitable vehicle such as liposomes, microparticles, or microcapsules. Cells of the present disclosure may also be supplied in the form of a pharmaceutical composition comprising an isotonic excipient, and prepared under conditions that are sufficiently sterile for human administration. General principles of medicinal formulations of cell compositions is found in *Cell Therapy: Stem Cell Transplantation, Gene Therapy, and Cellular Immunotherapy*, G. Morstyn & W. Sheridan eds., Cambridge University Press, 1996, and *Hematopoietic Stem Cell Therapy*, E.. Ball, J. Lister & P. Law, Churchill Livingstone, 2000, specifically incorporated herein by reference. Additionally, it may be desirable to administer a pharmaceutical composition containing a neuronal survival factor locally to the area in need of treatment, which may be achieved by, for example, local infuision during surgery, injection, a catheter means, or implant means, wherein such implant can be of a porous, non-porous, or gelatinous material, including membranes, such as silastic membranes or fibers.

The neuroprogenitor cells and terminally-differentiated neural cells of the present disclosure may be transplanted into a subject as either a substantially homogenous, nearly homogeneous, or heterogeneous cell population. A substantially homogenous cell population comprises greater than 75% of a single cell type, such as a dopaminergic neuron, more preferably greater than 90%, and most preferably greater than 95%-99%. A heterogeneous cell population will consist of two or more cell types mixed in a single cell population, for example dopaminergic neurons, serotonergic neurons, Schwann cells, oligodendrocytes, astrocytes, GABA neurons, and glial cells. The cells may also be genetically altered by methods well known to those of skill in the art to express or release trophic factors, growth factors, neuronal survival factors, or other therapeutic compounds in the damaged area of the brain, central nervous system, peripheral nervous system, or other tissues. Methods for protein expression are generally known to those of skill in the art of molecular biology, for example, see Sambrook, et al. 1989, Molecular Cloning: A Laboratory Manual $2^{nd}$ Ed. Cold Spring Harbor Laboratory Press, Cold Spring Harbor, N.Y., specifically incorporated herein by reference.

Graft placement, and the extent to which the graft reinnervates the striatum, are both important factors for the functional recovery of the mesostriatal dopaminergic system (Bjorklund et al., 1980, Brain Res. 199:307-33; Dunnett et al., 1981, Brain Res. 215:147-61; Dunnett et al., 1983, Acta Physiol. Scan. Suppl. 522:39-47; Nadaud et al., 1984, Brain Res. 304:137-41). While the transplantation site for dopaminergic graft has most often been in proximity to the vetitricular region because of the favorable cerebrospinal fluid (CSF) environment in those regions to provide for graft survival, the degree of dopaminergic degeneration in Parkinson's disease is more pronounced in the putamen than in the caudate nucleus (Bemhiemer et al., J. Neurol. Sci. 20:415-55; Nyberg et al., 1983, Neurochem. Pathol. 1: 93-202; Kish et al., 1986, Ann. Neurol. 20:26-31; DeLong & Georgopoulos, 1983, Handbook of Physiology, Section I: The Nervous System, Vol. 2, ed. Brookhard, Mountcastle, Geiger, pp. 1017-61, Bethesda, Md.: Am. Physiol. Soc.). Therefore, the putamen may be a more favorable site for dopaminergic grafts targeting motor disorders associated with Parkinson's disease.

The following examples are included to demonstrate preferred embodiments of the disclosure. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Human pluripotent ELSCs were cultured to form embryoid-like bodies (ELBs) by first proliferating and expanding the cells. Next, the cells were cultured on bacteriological plates having a non-adhesive surface that prevented attachment of the ELSCs, and stimulated differentiation of these cells. Briefly, ELSCs were dissociated by briefly exposing them to a 0.05% trypsin-EDTA solution, and subsequently cultured as a suspension culture in ES cell medium containing DMEM:F-12 or knockout DMEM, supplemented with 10-20% fetal calf serum, cord blood serum, or knockout serum replacement. The media was also supplemented with β-mercaptoethanol, L-glutamine, insulin, human transferrin, sodium selenite, but did not contain bFGF or hLIF. The cells were incubated in suspension culture for about 4 days and the media was changed every other day. The medium was changed by transferring the suspension of aggregates to a centrifuge tube, allowing the aggregates to settle down, aspirating the old medium, replacing it with fresh medium, and returning the aggregates and fresh medium to the culture dish.

At the end of 4 days, ELBs were collected by spinning down the aggregates at low speed (1000 rpm, 5 minutes) and resuspending the ELBs in the same ES cell medium described above. FIG. 1 shows this differentiation process using phase contrast micrographic pictures (10×). First, FIG. 1(a) shows ELSCs grown in culture after 15 passages. FIG. 1(b) shows ELBS, which formed after culturing ELSCs for 4 days in suspension culture. Finally, FIG. 1(c) shows initiation of differentiation from the ELBs.

To determine whether ELSCs disclosed herein can differentiate into dopaminergic neurons, ELBs derived from ELSCs were cultured for approximately 4-10 days in an appropriate medium and plated directly onto a suitable substrate with an extracellular matrix component such as poly-ornithine, laminin, or fibronectin. The ELBs were cultured in a suitable nutrient medium adapted to promote differentiation of the cells into neuroprogenitor cells. Then the cells were firrther cultured under conditions that encouraged differentiation and maturation into dopaminergic neurons.

The ELBs were cultured in serum-free defined medium composed of DMEM:F12 supplemented with N2 (1-15%) and B27 (1-20%), along with one or more antioxidants, such as DMSO (1-10%), Butylated hydroxyanisole (50-400 μM), and forskolin (5-20 μM), for initiation of neuronal induction. After 4-7 days of culture, one or a combination of growth factors such as Retinoic acid (20-80 ng/ml), GDNF (1-10 μg/ml), Shh (50-200 ng/ml), FGF-8 (50-200 ng/ml), or bFGF (10-50 ng/ml) were added to the medium to facilitate neuronal differentiation. The cells were grown in this medium for an additional 7-10 days. Changes in cell morphology of the cultured cells were observed within 48 hours. The percentage of responsive cells increased progressively with incubation under antioxidant and serum-free conditions. The neuroprogenitor cells were next grown in neuronal maturation media containing Neurobasal medium supplemented with N2 (1-15%), B27 (1-20%), GDNF (1-10 μg/ml), Retinoic acid (20-80 ng/ml), db-cAMP (10-200 μM), and IL-1β(1-5 μg/ml). Under these culture conditions, about 30-40% of the cells extended neurite processes and stained positive for β-tubulin, which evidenced their ability to form neurons. The growth factors present in the neuronal induction medium contribute to the overall increase in percentage of neuronal cells, and further induce these precursor cells to adopt the dopaminergic phenotype.

The dopaminergic cells generated according to the above protocols were evaluated both by the overall morphology of the cells, as well as the phenotypes identified by immunofluorescence. Immunofluorescence analysis was carried out at day 12 and day 25 of differentiation. First, the isolated cells were grown on 2-well chamber slides precoated with extracellular matrices, rinsed with PBS, and fixed for 10 minutes with 4% paraformaldehyde at room temperature. Next, the cells were permeabilized with 0.2% Triton X-100 in PBS for 5 minutes, blocked with 1% bovine serum albumin (BSA)/PBS for 2 hours, and incubated with a primary antibody (antibody dilutions were made in 1% BSA/Tris-buffered saline) overnight at 4° C.

The cells were stained with the following primary antibodies: early neuronal marker β-tubulin III (1:500); late neuronal marker Microtubule associated protein 2 (MAP-2) (1:200); gamma aminobutyric acid (GABA) (1:200); Glutamate (1:500); Nestin (1:50); Neurofilament (1:500); Tyrosine hydroxylase (TH) (1:800); Serotonin (1:500) and Oligodendrocyte (1:500). All primary antibodies were obtained from Chemicon Inc., USA. Next, the cells were incubated with the appropriate FITC-labeled secondary antibody. After each step, the cells were washed three times with PBS. The chamber slides were observed under a fluorescence microscope to evaluate the immunopositive areas. This immunofluorescence analysis demonstrated that many of the differentiated cells were immunoreactive to the neuron specific markers MAP-2, β-tubulin III, and Neurofilament, as well as the phenotype specific markers TH (marker for dopaminergic neurons), GABA (marker for GABAergic neurons), Glutamate (marker for glutamatergic neurons), and Serotonin (marker for serotonergic neurons). Only a few cells expressed the non-neuronal marker O4, which is present in Oligodendrocytes (glial cells).

The functional capacity of ELSC-derived dopaminergic neurons to produce dopamine was evaluated by directly measuring the extracellular dopamine levels using Reverse Phase HPLC (RP-HPLC). The concentration of dopamine detected in culture supernatant was determined by comparison with a standard solution of dopamine injected into the column immediately before and after each analysis. Approximately $5 \times 10^6$ cells were trypsinized and pelleted by centrifugation. The cells were then sonicated in cold 1N perchloric acid with antioxidants (0.2 g/l sodium metabisulphite), and centrifuged at 15,000 rpm/min for 20 minutes at 4° C. Next, the culture supernatant was immediately stabilized with 7.5% orthophosphoric acid and sodium metabisulphite, and stored at −70° C. for subsequent determination of the extracellular dopamine concentration by RP-HPLC. Dopamine levels in the culture supernatant (48 hours after the last medium change) at day 25 of differentiation was approximately 70 μg/ml.

EXAMPLE 2

High Efficiency Generation of Dopaminergic Neurons From ELSCs

Figure 2:
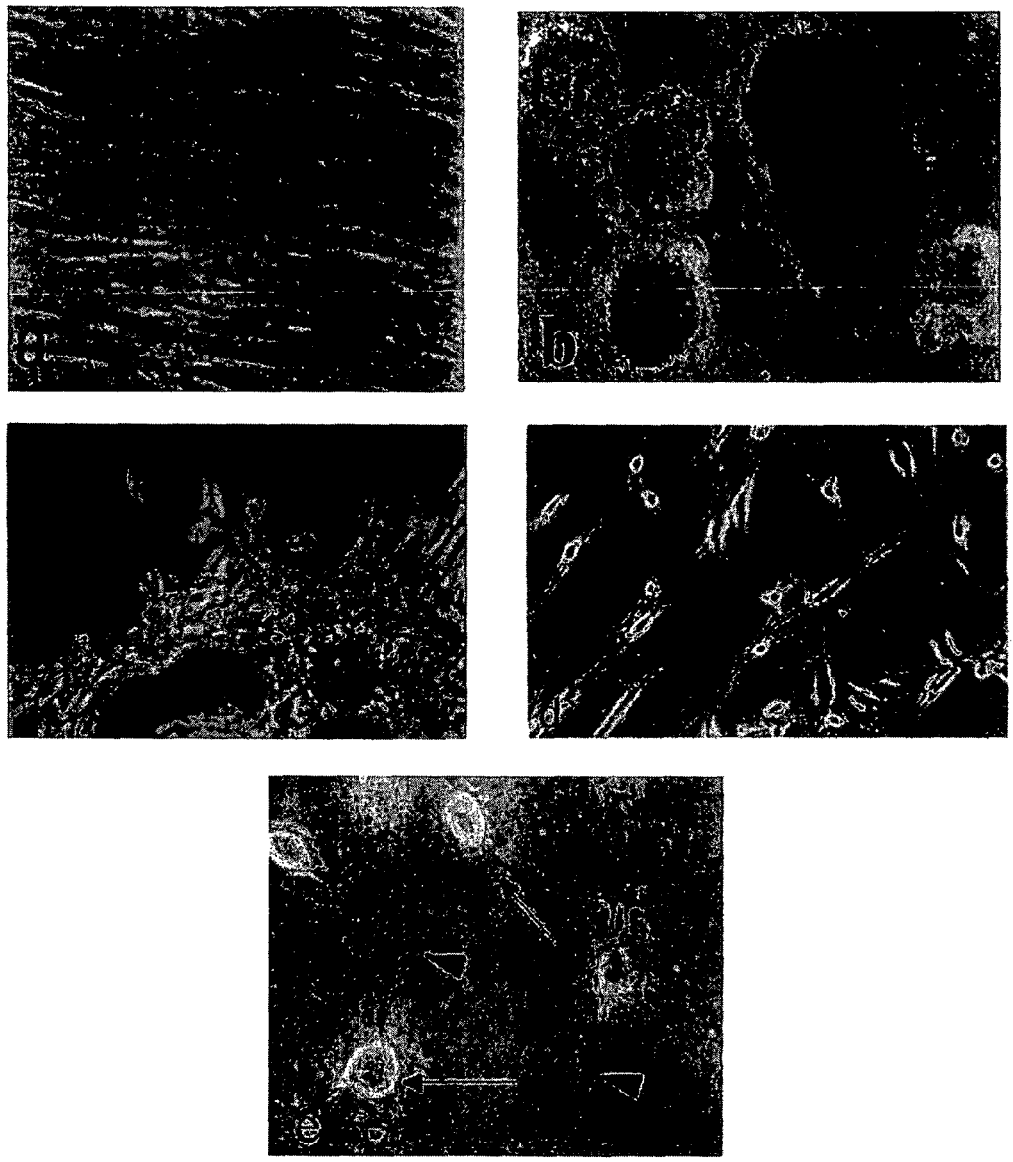
FIG. 2. Phase contrast pictures showing in vitro differentiation of neuronal cells from ELSCs derived from corneolimbal tissue: (a) Undifferentiated ELSCs isolated from limbal tissue which exhibit fibroblast-like morphology (10×); (b) Undifferentiated ELSCs grown in suspension culture to generate free-floating clusters of cells resembling embryoid bodies (10×); (c) Embryoid-like bodies (ELBs) generated from ELSCs differentiating into neuroprogenitor cells (10×); (d) and (e) After 4 weeks post-neuronal differentiation, the cells formed neuronal-like structures (arrow) with fine neuronal networks (arrow heads), 10× magnification and 20× magnification, respectively.

Neuroprogenitor cells prepared according to the methods disclosed herein can be further differentiated into high proportions of dopaminergic neurons. In a specific embodiment, the neuroprogenitor cells are differentiated in Neurobasal-A medium, supplemented with 0.5-2% N2, 1-4% B27, GDNF (10-30 ng/ml), Retinoic acid (15-27 ng/ml), db-cAMP (30-60 ,μm) and Interleukin-1β(175-230 pg/ml).(FIG. 2(c)-2(e)).

Derivation of Dopaminergic Neurons Without Formation of ELBs

The ELSCs disclosed herein, which were derived from corneo-limbal tissue, can be plated onto extracellular matrix coated plates, preferably coated with poly-L-ornithine and laminin. The cells are then cultured under conditions to encourage further differentiation of the cells into neural precursor cells. For example, the cells may be cultured in serum-free expansion medium, preferably comprising a minimal essential medium, such as Neural basal medium, and is supplemented with neuronal inducing agents such as N2 and B27. The expansion media also preferably includes one or more growth factors, such as Retinoic acid, db-cAMP and Interleukin-1β. To characterize the differentiated cell types generated according to these methods, overall morphology of the cells was observed, the presence or absence of neuronal markers was assessed by immunofluorescence microscopy, and gene expression analysis was performed via RT-PCR.

Molecular Characterization of Dopaminergic Neurons Derived From ELSCs

Figure 3:
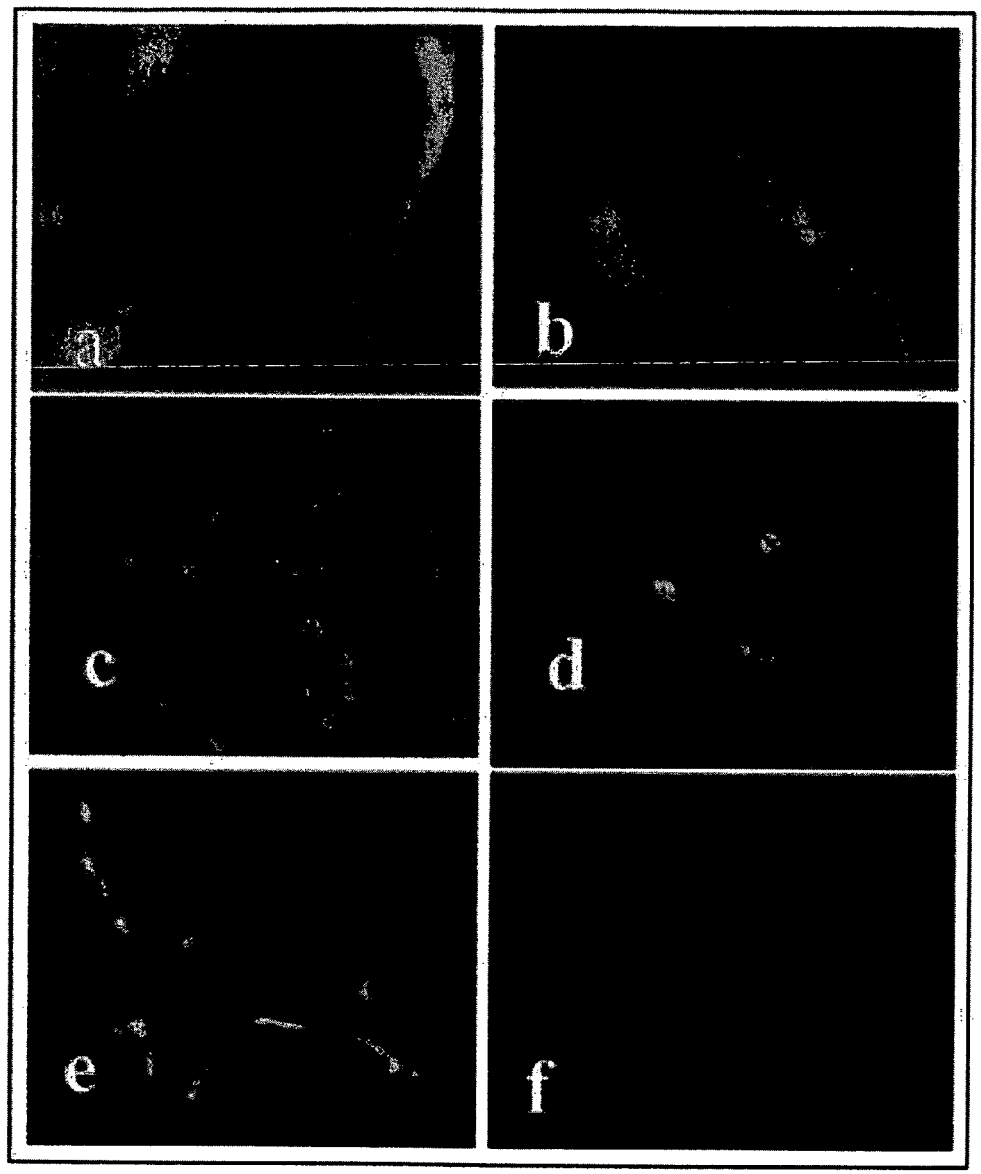
FIG. 3. Cellular characterization of neuronal cells differentiated from ELSCs. Differentiated cells were positive for the following neuron-specific markers: (a) Nestin, (b) Neurofilament NF 200 (counterstained with DAPI), (c) MAP-2, (d) TH (specific for dopaminergic neurons); (e) serotonin; and (f) O4 (an oligodendrocyte marker).

Immunofluorescence analysis preferably was performed 15 days after neuronal differentiation was induced. Immunofluorescence of the differentiated cells derived from ELSCs was performed to identify neuronal cells immunopositive for neuronal markers. Cells were grown in 2-well chamber slides (Becton Dickinson, USA), fixed in freshly prepared 4% paraformaldehyde, and permeabilized with 0.2 % Triton X-100 in PBS. Non-specific binding sites were blocked with 1% bovine serum albumin in PBS. The cells were then incubated overnight at 4° C. with primary antibody, washed 3 times in PBS, incubated with appropriate fluorescently labeled secondary antibodies for 2 hours, and counterstained with DAPI (1ug/ml; Sigma). Cells were embedded in immunofluor mounting medium and observed using a fluorescence microscope (Nikon Eclipse E600). See FIG. 3. The following antibodies were utilized: anti-Nestin (1:200), anti-NCAM (1:200), anti-Neurofilament 200kDa (NF200, 1:200), anti-Tyrosine hydroxylase (TH, 1:1000), anti-MAP-2 (1:200), anti-serotonin (1:200) and anti-Oligodendrocyte (1:200). All primary antibodies were procured from Chemicon, and all secondary antibodies were procured from Molecular Probes. Approximately 40% of the differentiated cells were positive for TH.

The gene expression profiles of differentiated cells were analyzed by RT-PCR. Differentiated cells were collected and pelleted, and total cellular RNA was extracted using the trizol method or the the RNeasy Qiagen kit. The isolated RNA was stored at −20° C. Total cellular RNA was treated with RNase-free RQ DNase (Promega Corp., Madison, Wis.) to remove all DNA. cDNA was synthesized from the isolated total RNA using Moloney Leukemia Virus Superscript II Reverse Transcriptase according to the manufacturer's instructions. Random hexamer primers (GIBCO/BRL) were used to prime the reverse transcriptase (RT) reactions. The cDNA synthesized by this RT reaction was subjected to PCR amplification using different sets of specific primers to determine which genes were expressed in the collected cells. The primers were designed to identify mRNAs expressed in glial cells or neuronal cells, specifically dopaminergic neurons. The ubiquitously expressed housekeeping gene, GAPDH, served as the internal control. These PCR reactions were carried out using 10% of the total first strand reaction (cDNA synthesized by RT) as the template and using standard PCR conditions, which are well known to those of skill in the art. The general cycling parameters used to amplify DNA products were as follows: (1) Denaturation of the template cDNA at 94°C. for 30 seconds; (2) annealing. the primers at 55-65° C. for 1 minute, depending on the primers used; and (3) incubating the reaction at 72° C. for 1 minute; and (4) repeating steps 1-3 (cycles) between 25 and 40 times.

After the PCR reaction, the products were electrophoretically separated on an agarose gel. The expression of TH, β-Tubulin, Nurr1, En-1, GFAP, and GAPDH were analyzed by RT-PCR using the primers described in Table 1.

TABLE 1

| Gene | Primer Sequence | |
|---|---|---|
| TH (417 bp) | TGT CAG AGC AGC CCG AGG TC | (SEQ ID NO: 1) |
|  | CCA AGA GCA GCC CAT CAA AG | (SEQ ID NO: 2) |
| β-tubulin (317bp) | GGA ACA TAG CCG TAA ACT GC | (SEQ ID NO: 3) |
|  | TCA CTG TGC CTG AAC TTA CC | (SEQ ID NO: 4) |
| En-1 (390bp) | TGG TCA AGA CTG ACT CAC AGC A | (SEQ ID NO: 5) |
|  | TCT CGT CTT TGT CCT GAA CCG T | (SEQ ID NO: 6) |
| Nurr1 (255bp) | TGA AGA GAG CGG AGA AGG AGA T | (SEQ ID NO: 7) |
|  | TCT GGA GTT AAG AAA TCG GAG CT | (SEQ ID NO: 8) |
| GFAP (100bp) | AGC AGC CTG AGG AAA CTC AA | (SEQ ID NO: 9) |
|  | CTC CAC ATC CCT GAT TCC TG | (SEQ ID NO: 10) |
| GAPDH (890bp) | TGA AGG TCG GAG TCA ACG GAT TTG GT | (SEQ ID NO: 11) |
|  | CAT GTG GGC CAT GAG GTC CAC CAC A | (SEQ ID NO: 12) |

Figure 4:
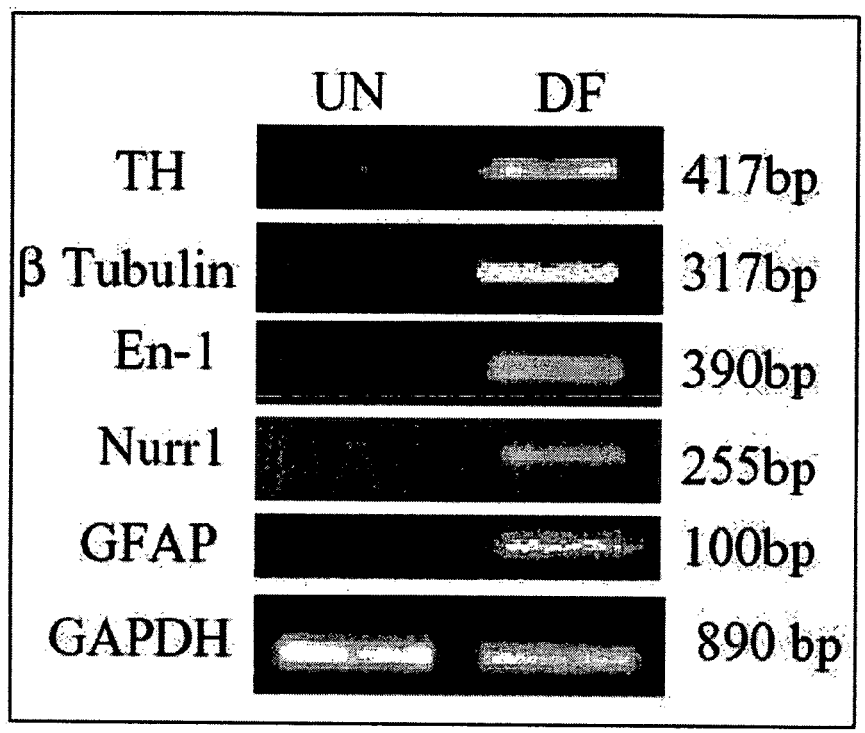
FIG. 4. Expression of genes specific to midbrain development in neurons derived from ELSCs. Reverse Transcriptase Polymerase Chain Reaction (RT-PCR) analysis demonstrated that differentiated cells express genes specific to midbrain development, namely TH, β-tubulin, Nurr1, and En-1, as well as GFAP, a marker for glial cells. The ELSCs (undifferentiated "UN") did not express any of these markers. GAPDH served as the internal control.

The above analysis by RT-PCR demonstrated that many differentiated cells expressed neuronal markers including TH, β-tubulin, Nurr1, En-1 along with GFAP, a marker for glial cells. GAPDH served as the internal control. See FIG. 4.

Functional Characterization of Dopaminergic Neurons Derived From ELSCs

As another means of identifying dopaminergic neurons, reverse phase high performance liquid chromatography (RP-HPLC) was employed to determine whether the neuronal cells derived from ELSCs secrete dopamine into the culture supernatant.

Figure 5:
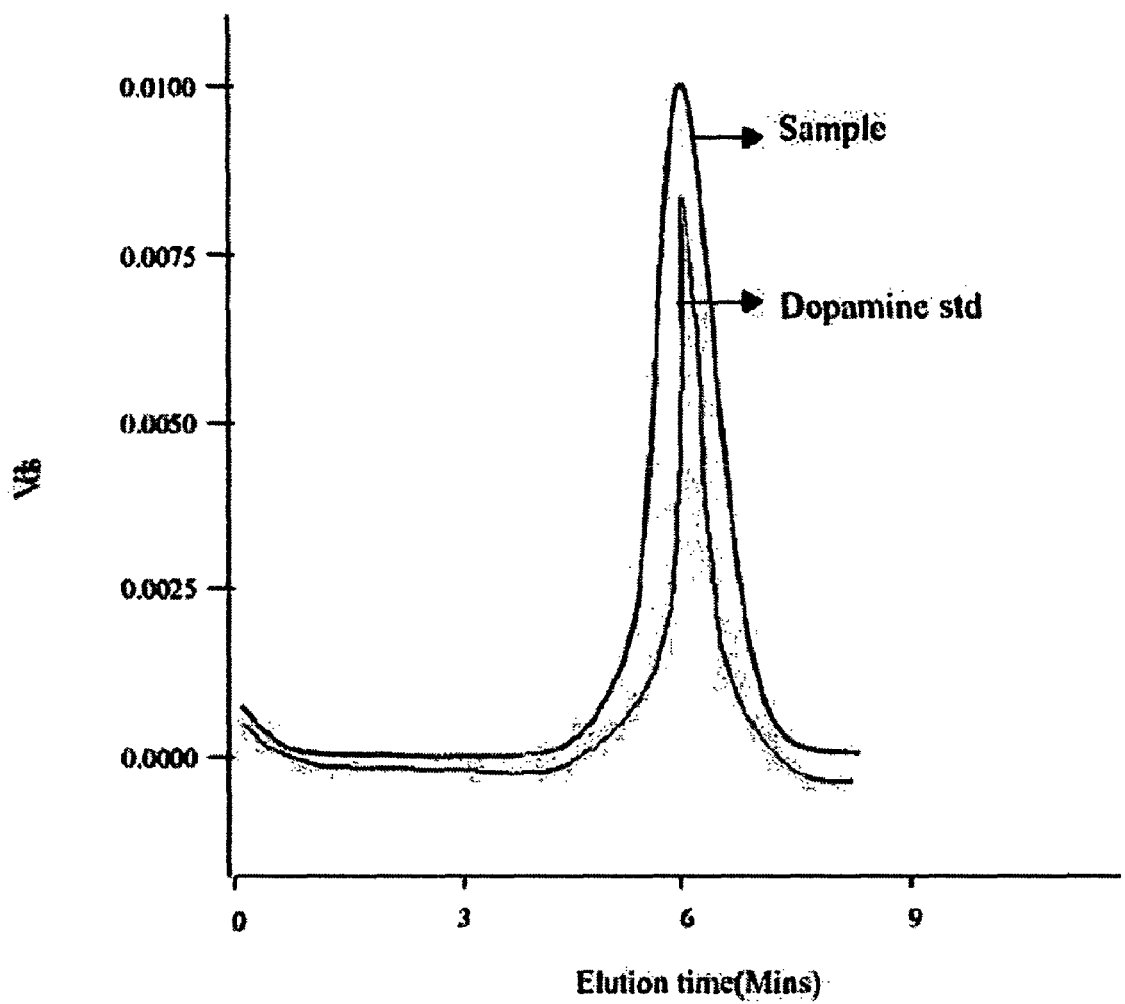
FIG. 5. Functional analysis of terminally differentiated dopaminergic neurons generated from ELSCs. Reverse-phase HPLC demonstrated that dopaminergic neurons derived from ELSCs secrete dopamine. The dopamine secreted by dopaminergic neurons derived from ELSCs exhibited the same elution time as the dopamine standard, an indication that the dopamine produced by the ELSC-derived neurons is molecularly identical to the dopamine standard.
Figure 6:
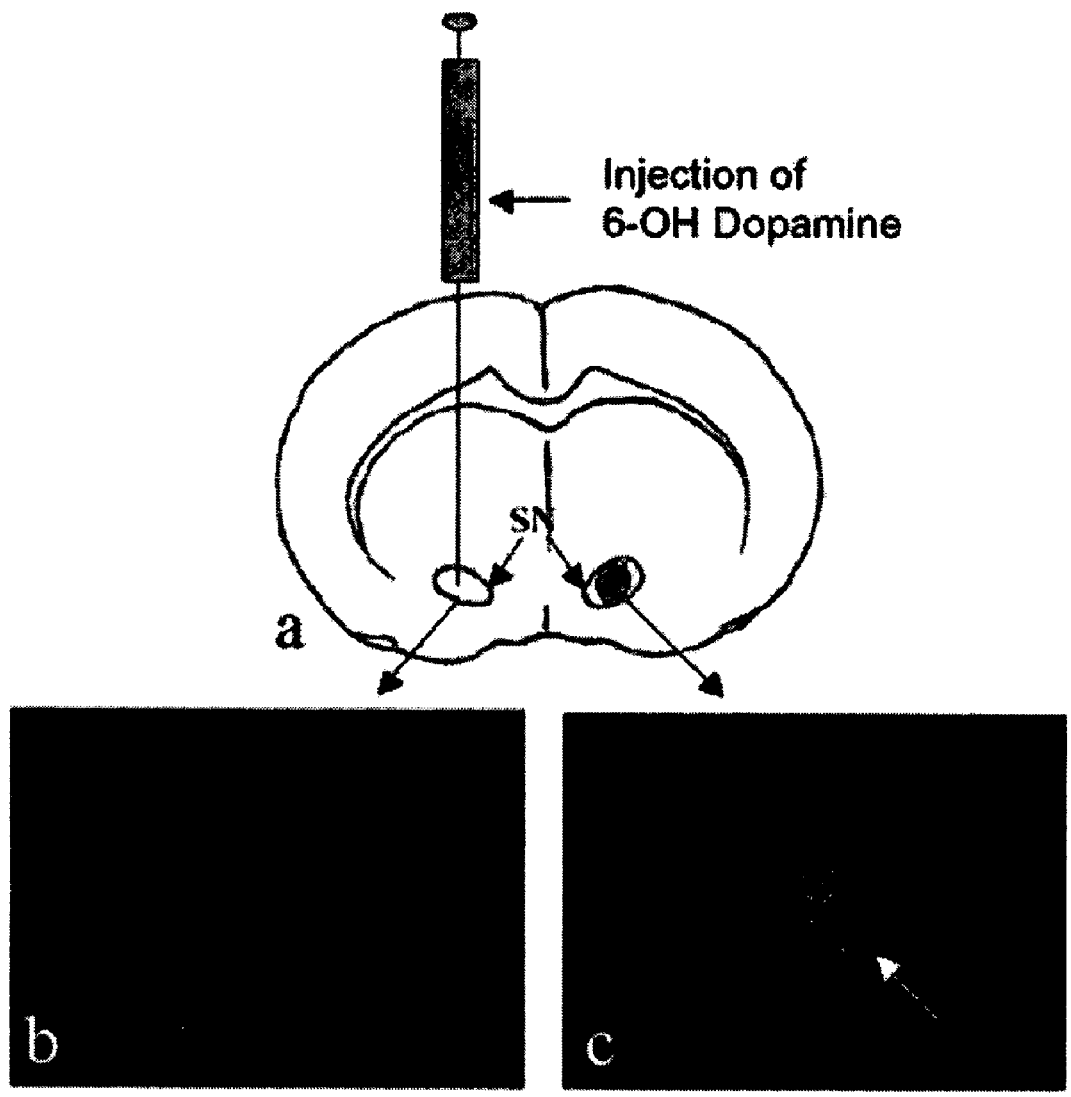
FIG. 6. A rat model of Parkinson's disease generated by 6-hydroxydopamine (6-OHDA) injection into the substantia nigra region. (a) Diagram of transverse section of rat brain illustrating 6-OHDA injection into the substantia nigra region (SN); the uninjected substantia nigra served as a negative control; (b) Complete degeneration of dopaminergic neurons in the substantia nigra region was demonstrated by the absence of TH as demonstrated by immunofluorescence (10×); (c) Immunofluorescence demonstrated that the neurons in the uninjected substantia nigra were positive for TH (10×).

Aluminum absorption, equipment and HPLC analysis of dopamine have been described previously (Studer et al., 1998, Nature Neurosci. 1:290-295; and Studer et al., 1996, Brain Res. Bull. 41:143-150). RP-HPLC was used to ascertain the amount of dopamine secreted into the culture supernatant by the differentiated cells after 15 days of differentiation. Immediately following collection, culture supernatants were stabilized with orthophosphoric acid/7.5% metabisulphite (0.22mg/ml) and stored at −80° C. until HPLC analysis. HPLC peaks were authenticated by re-analyzing samples in the presence of a known quantity of standard. See FIG. 5. Reverse-phase HPLC demonstrated that dopaminergic neurons derived from ELSCs secrete dopamine. The dopamine secreted by dopaminergic neurons derived from ELSCs exhibited the same elution time as the dopamine standard, an indication that the dopamine produced by the ELSC-derived neurons is molecularly identical to the dopamine standard.

EXAMPLE 3

Use of ELSCs in Cell Replacement Therapy

Figure 7:
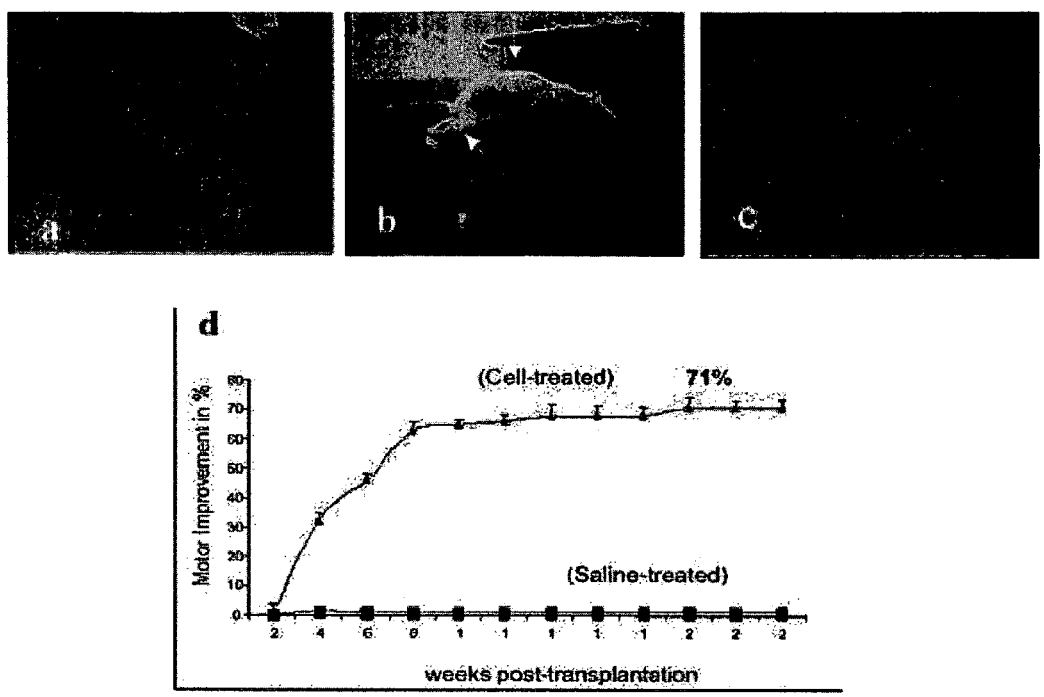
FIG. 7. Behavioral analysis of rats following transplantation of ELSC-derived neuroprogenitor cells. (a) Prior to 6-OHDA, rats exhibited normal walking behavior, coordinated body movement, and posture; (b) Lack of coordination in forelimb and hindlimb movements ten-weeks after administration of 6-OHDA; rats also exhibited posture deformities, and this rat developed a severe ipsilateral circling behavior; (c) Recovery from motor abnormalities six-months following transplantation of neuroprogenitor cells; this rat displayed a significant improvement in posture, and the abnormal ipsilateral circling was almost completely corrected; (d) Transplantation of neuronal progenitor cells corrected the ipsilateral circling defect observed in 6-OHDA-injected rats. While no improvement was observed in saline-treated rats, evidence of recovery was apparent two-weeks post-transplantation in rats receiving the ELSC-derived neuroprogenitor cells.

To generate an animal model of Parkinson's disease, rats were treated with 6-OHDA. Treated rats exhibiting ipsilateral circling behavior; which is moving in a circular pattern more than 20 times per minute in the same direction, were selected as Parkinson-induced rats to be used for further experimentation. 6-OHDA-treated rats represent the most frequently used hemiparkinson model, likely because 6-OHDA treatment consistently promotes asymmetrical and quantifiable motor behavior abnormalities, but does not promote the low survivability and increased need for medical care characteristic of other Parkinson's animal models (Cenci et al., 2002, 23:105-9). Most of the rats treated with 6-OHDA exhibited ipsilateral circling while rats treated with saline did not exhibit this behavior. See FIG. 7.

To determine if cell transplantation therapy using neuroprogenitor cells derived from ELSCs isolated from corneolimbus tissue could alleviate parkinsonism symptoms in the rat hemiparkinson model, about 1.2 million neuroprogenitor cells/rat were transplanted into 6 rats which exhibited stable deterioration of motor functions and a significant ipsilateral turning behavior, namely rats that performed at least 20 ipsilateral rotations per minute. Each rat was anesthetized with ketamine (50 mg/kg i.p) and valium (30 mg/kg i.p/) and immobilized in a stereotaxic frame (Stoelting Co. USA). The substantia nigra of each rat was injected with 1.2 million in 50 µl neuroprogenitor cells using a 28-guage syringe and a rate of 2 µl/min. Cell transplantation was performed using a motorized microinjector (Stoelting Co., USA). Control rats (n=6) underwent the same surgical procedure but were injected with saline rather than neuroprogenitor cells. Because the rats were injected with neuroprogenitor cells derived from human ELSCs, each rat received an injection Cyclosporine A (15 mg/kg; Sigma Chemicals, USA) to prevent rejection of the neuroprogenitor cells.

Behavioral analysis was performed on rats that received neuroprogenitor cells and control rats injected with saline. A standard t-test analysis was used to compare rotational behavior observed before transplantation to rotational behavior observed at 4, 6, 8, and 10 weeks post-translation. Significance values were corrected using the Bonferroni method. Differences were considered statistically significant when P <0.05. Data are presented as mean ±SEM. Based on the rate of ispilateral circle behavior, approximately 70% of the rats that underwent cell transplantation therapy exhibited a significant improvement in motor behavior.

Figure 8:
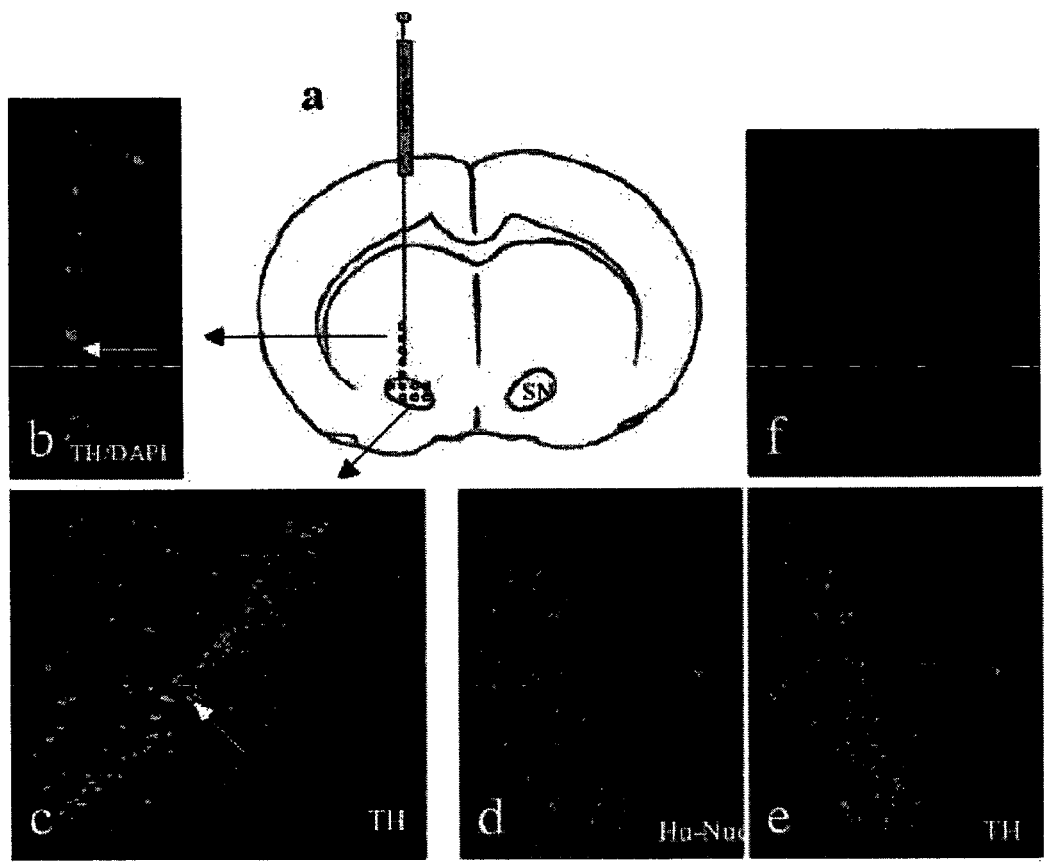
FIG. 8. Immunohistochemistry of brain sections of rats which were treated with ELSC-derived neuroprogenitor cells twenty-four weeks after previously being induced to develop symptoms of Parkinson's disease by 6-OHDA injection. (a) Diagram illustrating the substantia nigra (SN), which is the site of 6-OHDA injection and the site of neuroprogenitor cell transplantation; (b) Transverse section of rat brain demonstrating expression of TH at the site of injection; (c) TH expression demonstrated that the transplanted neuroprogenitor cells differentiated into dopaminergic neurons; (d) Transplanted ELSC-derived neuroprogenitor cells (stained using an anti-human nuclei antibody) in a transverse section of rat brain; (e) Colocalization of anti-TH and anti-human nuclei antibodies was observed; (f) Negative control demonstrating that prior to transplantation, a transverse section of rat brain is negative for anti-human nuclei.

Immunohistochemistry demonstrated that the injected neuroprogenitor cells survived in the rat brains and differentiated into dopaminergic neurons by 16 weeks post-transplantation. 16 weeks following transplantation, rats were anesthetized with ketamine (50 mg/kg i.p) and valium (30 mg/kg i.p) and then perfused with saline followed by 4% paraformaldehyde. The brains were removed, equilibrated in 20% sucrose in PBS overnight at room temperature, embedded in OCT compound, frozen in liquid Nitrogen, sectioned using a cryostat, and the 10 µm sections were mounted onto slides coated with poly-L-lysine. The slides were dipped in citrate buffer, heated in a microwave for 30 seconds, and permeabilized with 0.2 % Triton X-100 in PBS. Non-specific binding sites were blocked using 1% bovine serum albumin in PBS. The sections were then incubated overnight at 4° C. with anti-TH and anti-human nuclei antibodies or appropriate negative controls. Sections were washed 3 times in PBS and then incubated with FITC-conjugated secondary antibody for 2 hours. The sections were then counterstained with DAPI (1ug/ml; Sigma), embedded in immunofluor mounting medium, and observed using a fluorescence microscope. See FIG. 8. To determine the origin of transplanted TH-positive cells, colocalization of anti-TH and anti-human nuclei antibodies was observed. Approximately 80% of the injected cells that survived in the rat brain differentiated into TH-positive cells.

No improvement of motor function was observed during the first two weeks following transplantation of neuroprogenitor cells (FIG. 7(d)). After three weeks, rats that received transplanted neuroprogenitor cells exhibited a significant reduction in ipsilateral circling. The average recovery observed was 71.76±2.55 %, based on reduced ipsilateral circling. Motor behaviors continued to improve until 8 to 9 weeks after transplantation (FIG. 7(d)). The improved motor behaviors persisted, with no observable deterioration, 6 months after transplantation of neuroprogenitor cells (FIG. 7(c) and 7(d)). The reduced ipsilateral circling was the most prominent improvement observed in the neuroprogenitor cell-transplanted rats, but significant improvements were also observed in forelimb and hindlimb motility and body curvature. In the Parkinson-induced rats treated with saline only, no improvement of behavioral functions was observed, indicating that the behavioral improvements in the neuroprogenitor cell-transplanted rats was due to neural cell transplantation.

The area of the brain into which neuroprogenitor cells were injected was analyzed to determine if injected cells had differentiated into dopaminergic neurons. Almost all transplanted cells expressed TH, indicating that the injected neuroprogenitor cells had become dopaminergic neurons (FIG. 8(b) and 8(c)). Since human neuroprogenitor cells were transplanted into rats with parkinsonism, transplanted neuroprogenitor cells were identified by positive immunolabeling with anti-human nuclei. As demonstrated in FIG. 8(d), TH-positive cells were also immunopositive for anti-human nuclei, indicating that the dopaminergic neurons were derived from the transplanted human neuroprogenitor cells. It appeared that all TH-positive cells also had a human nuclei. The rats treated with saline-only did not exhibit any cells immunopositive for anti-human nuclei, which demonstrated that the transplanted cells were of human origin in rats transplanted with neuroprogenitor cells.

Many attempts have been made to use cell transplantation to alleviate parkinsonism in animal models. An early approach employed direct transplantation of undifferentiated stem cells into the brain, but this approach proved unsuccessful because only 5-10% of the transplanted cells survived, and there was a high risk of tumor formation. Another approach employed transplantation of terminally differentiated dopaminergic neurons into the brain of animals with parkinsonism, but cell survival was very limited, with 90-95% of the cells losing viability shortly after transplantation. While it is unclear why transplanted neuronal cells exhibit such a significant loss of cell viability post-transplantation, recent reports suggest that transplantation of glial cells along with neuroprogenitor cells may improve the survival rate of transplanted cells. The methods described in the present disclosure demonstrate that transplanted neuroprogenitor cells derived from ELSCs isolated from human corneo-limbal tissue display significantly improved cell viability post-transplantation. Even 6 months after transplantation, more than 50% of the transplanted cells remained viable and displayed characteristics of functional dopaminergic neurons. The high rate of survival of transplanted cells may be responsible for the observed improved motor function in Parkinson's rats injected with neuroprogenitor cells as disclosed herein.

The described histological examination of rat brains injected with neuroprogenitor cells demonstrated that the observed behavioral recovery was due to transplanted neuroprogenitor cells. These findings emphasize the therapeutic potential of the neuroprogenitor cells of the present disclosure as an autologous cell therapy in the treatment of Parkinson's disease.

To analyze the tumorigenic potential of ELSCs derived from human corneo-limbal tissue, undifferentiated ELSCs (5 million cells/animal) were injected intramuscularly into the NMRl nu/nu mouse. The transplanted animals were assessed for a period of 12-15 weeks and were subsequently sacrificed for histological analysis and immunohistochemical analysis. ELSCs isolated from corneo-limbal tissue did not promote any tumor formation in the NMRl nu/nu mouse, while mice injected with NTera2 cells, a human carcinoma cell line, developed tumors within 8-10 weeks post-injection at the injection site. Even after six-months, not a single animal injected with ELSCs exhibited any tumor-like structures in or around the injection site. In addition, because neuroprogenitor cells were transplanted into the substantia nigra, these cells were examined to determine whether they migrated to other parts of the brain. No migration of cells to areas outside of the substantia nigra was observed even 6-months post-transplantation.

Sixteen weeks post transplantation rats were anesthetized with ketamine (50 mg/kg i.p) and valium (30 mg/kg i.p). and then perfused with saline followed by 4% paraformaldehyde. The brains were removed and equilibrated in 20% sucrose in PBS overnight at room temperature, embedded in OCT compound, and frozen in liquid Nitrogen. Sections were cut into 10 µM thick slices using a cryostat and placed on poly L lysine coated slides. The sections were dipped in citrate buffer and heated in a microwave for 30 seconds. The sections were permeabilized with 0.2 % Triton X-100 in PBS. The non-specific binding sites were blocked with 1% bovine serum albumin in PBS. The sections were then incubated overnight at 4° C. with anti-TH and anti-human Nuclei antibodies along with negative controls, respectively. After washing thrice with PBS, sections were incubated with secondary antibody conjugated with FITC for 2 hours. In order to confirm the origin of transplanted TH-positive cells, colocalisation with anti-human nuclei was done. The sections were counterstained with DAPI (1ug/ml; Sigma), embedded in immunoflour mounting medium, and observed under a fluorescence microscope FIG. 8. These results suggests that neuroprogenitor cells disclosed herein can differentiate into dopaminergic neurons in vivo and restore motor function in rats with parkinsonism in the absence of undesired effects such as tumor formation and cell migration to areas outside of the substantia nigra.

The capacity of human neuroprogenitor cell derived from ELSCs isolated from corneo-limbal tissue to form functional dopaminergic neurons in vitro and in vivo, as well as restore the motor abnormalities associated with Parkinson's disease in a rat model, demonstrate the potential utility of these cells in treating Parkinson's patients. The six-month long survivability of transplanted cells in the host brain without forming a tumor demonstrates safe and clinically viable cell transplantation. These findings also emphasize the potential of the neuroprogenitor cells disclosed herein for the treatment of other neurological disorders.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents that are chemically or physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A population of neural precursor cells in an in vitro culture generated by differentiating human pluripotent embryonic-like stem cells (ELSCs) derived from human corneoscleral limbus tissue, and isolated based on the expression of SSEA-4, keratin growth factor ("KGF"), collagen-I and p63, into neural precursor cells.

2. The cell population of claim 1, wherein the ELSCs:
   i) are capable of proliferating in an in vitro culture;
   ii) maintain the potential to differentiate into cells of endoderm, mesoderm or ectoderm lineage in culture; and
   iii) are capable of forming embryoid-like bodies when placed in suspension culture.

3. The cells of claim 1, wherein said population of neural precursor cells also expresses keratin.

* * * * *

SEQUENCE LISTING

```
<160> NUMBER OF SEQ ID NOS: 12

<210> SEQ ID NO 1
<211> LENGTH: 20
<212> TYPE: DNA
<213> ORGANISM: Homo sapiens

<400> SEQUENCE: 1
tgtcagagca gcccgaggtc                                             20

<210> SEQ ID NO 2
<211> LENGTH: 20
<212> TYPE: DNA
<213> ORGANISM: Homo sapiens

<400> SEQUENCE: 2
ccaagagcag cccatcaaag                                             20

<210> SEQ ID NO 3
<211> LENGTH: 20
<212> TYPE: DNA
<213> ORGANISM: Homo sapiens

<400> SEQUENCE: 3
ggaacatagc cgtaaactgc                                             20
```

```
<210> SEQ ID NO 4
<211> LENGTH: 20
<212> TYPE: DNA
<213> ORGANISM: Homo sapiens

<400> SEQUENCE: 4
tcactgtgcc tgaacttacc                                                   20

<210> SEQ ID NO 5
<211> LENGTH: 22
<212> TYPE: DNA
<213> ORGANISM: Homo sapiens

<400> SEQUENCE: 5
tggtcaagac tgactcacag ca                                                22

<210> SEQ ID NO 6
<211> LENGTH: 22
<212> TYPE: DNA
<213> ORGANISM: Homo sapiens

<400> SEQUENCE: 6
tctcgtcttt gtcctgaacc gt                                                22

<210> SEQ ID NO 7
<211> LENGTH: 22
<212> TYPE: DNA
<213> ORGANISM: Homo sapiens

<400> SEQUENCE: 7
tgaagagagc ggagaaggag at                                                22

<210> SEQ ID NO 8
<211> LENGTH: 23
<212> TYPE: DNA
<213> ORGANISM: Homo sapiens

<400> SEQUENCE: 8
tctggagtta agaaatcgga gct                                               23

<210> SEQ ID NO 9
<211> LENGTH: 20
<212> TYPE: DNA
<213> ORGANISM: Homo sapiens

<400> SEQUENCE: 9
agcagcctga ggaaactcaa                                                   20

<210> SEQ ID NO 10
<211> LENGTH: 20
<212> TYPE: DNA
<213> ORGANISM: Homo sapiens

<400> SEQUENCE: 10
ctccacatcc ctgattcctg                                                   20

<210> SEQ ID NO 11
<211> LENGTH: 26
<212> TYPE: DNA
<213> ORGANISM: Homo sapiens

<400> SEQUENCE: 11
tgaaggtcgg agtcaacgga tttggt                                            26
```

```
<210> SEQ ID NO 12
<211> LENGTH: 25
<212> TYPE: DNA
<213> ORGANISM: Homo sapiens

<400> SEQUENCE: 12
catgtgggcc atgaggtcca ccaca                                              25
```